(12) United States Patent
Hayakawa et al.

(10) Patent No.: US 7,598,038 B2
(45) Date of Patent: Oct. 6, 2009

(54) METHOD FOR ESTIMATING END USE QUALITIES OF WHEAT AT GROWTH STAGE

(75) Inventors: Katsuyuki Hayakawa, Saitama (JP); Yosuke Kikuchi, Saitama (JP); Hirofumi Motoi, Saitama (JP); Kouji Uchida, Shiga (JP); Masahiro Kinugasa, Shiga (JP)

(73) Assignees: Nisshin Seifun Group Inc., Tokyo (JP); Oriental Yeast Co., Ltd., Tokyo (JP)

( * ) Notice: Subject to any disclaimer, the term of this patent is extended or adjusted under 35 U.S.C. 154(b) by 275 days.

(21) Appl. No.: 11/662,781

(22) PCT Filed: Sep. 15, 2005

(86) PCT No.: PCT/JP2005/017009

§ 371 (c)(1),
(2), (4) Date: Mar. 14, 2007

(87) PCT Pub. No.: WO2006/030846

PCT Pub. Date: Mar. 23, 2006

(65) Prior Publication Data

US 2008/0213758 A1 Sep. 4, 2008

(30) Foreign Application Priority Data

Sep. 17, 2004 (JP) ............... 2004-271391

(51) Int. Cl.
C12Q 1/68 (2006.01)
C12P 19/34 (2006.01)
C07H 21/02 (2006.01)
C07H 21/04 (2006.01)
C12M 1/34 (2006.01)
C12M 3/00 (2006.01)

(52) U.S. Cl. ............... 435/6; 435/91.2; 435/287.1; 536/23.1; 536/24.3

(58) Field of Classification Search ............... None
See application file for complete search history.

(56) References Cited

U.S. PATENT DOCUMENTS 5,474,796 A * 12/1995 Brennan ............... 427/2.13

FOREIGN PATENT DOCUMENTS

| JP | 06-125669 | 5/1994 |
|---|---|---|
| JP | 09-191819 | 7/1997 |
| JP | 2000-516097 | 12/2000 |
| JP | 2003-284598 | 10/2003 |

| WO | 98/07747 | 2/1998 |

OTHER PUBLICATIONS

S. B. Altenbach, Quantification of individual low-molecular-weight glutenin subunit transcripts in developing wheat grains by competitive RT-PCR, Theor Appl Genet, 1998, vol. 97, pp. 413-421.
David C. Baulcombe, et al., A novel wheat α-amylase gene (α-Amy3), Mol Gen Genet, 1987, vol. 209, pp. 33-40.
P.I. Payne, et al., Structural and Genetical Studies on the High-molecular-weight Subunits of Wheat Glutenin, Theor. Appl. Genet., vol. 60, 1981, pp. 229-236.
Peter I. Payne et al., Correlation Between the Inheritance of Certain High-molecular Weight Subunits of Glutenin and Bread-making Quality in Progenies of Six Crosses of Bread Wheat, J.Sci. Food Agric., 1981, vol. 32, pp. 51-60.
R.B. Flavell, et al., Genetic Variation in Wheat HMW Glutenin Subunits and the Molecular Basis of Bread-Making Quality, Bio/Technology, vol. 7, Dec. 1989, pp. 1281-1285.
Francisco Barro, et al., Transformation of wheat with high molecular weight subunit genes results in improved functional properties, Nature Biotechnology, vol. 15, Nov. 1997, pp. 1295-1299.
P. Greenwell et al., a Starch Granule Protein Associated with Endosperm Softness in Wheat, Cereal Chemistry, vol. 63, No. 4, 1986, pp. 379-380.
Laurence Dubreil, et al., Effect of Puroindolines of the Breadmaking Properties of Wheat Flour, Cereal Chemistry, vol. 75(2):pp. 222-229 (1998).
C.J. Jolly, et al., Characterisation of the wheat Mr 15000 "grain-softness protein" and analysis of the relationship between its accumulation in the whole seed and grain softness, Theor Appl Genet, 1993, vol. 86, pp. 589-597.
Supplemental European Search Report issued Dec. 19, 2008 in EP 05783246.1.
Perrotta, C. et al., "Analysis of mRNAs from Ripening Wheat Seeds: the Effect of High Temperature", *Journal of Cereal Science*, (1998), 27: 127-132.
Altenbach, S. B. et al., "Transcript profiles of genes expressed in endosperm tissue are altered by high temperature during wheat grain development", *Journal of Cereal Science*, (2004), 40: 115-126.
Examiner's Report issued Jan. 7, 2009 in Australian Patent Application No. 2005283442.
Wilson, I. et al., "A transcriptomics resource for wheat functional genomics", *Plant Biotechnology Journal*, (2004), 2:495-506.

* cited by examiner

*Primary Examiner*—Teresa E Strzelecka
(74) *Attorney, Agent, or Firm*—Wenderoth, Lind & Ponack, L.L.P.

(57) ABSTRACT

The invention provides a means for estimating the end use qualities of wheat flour that will be obtained in the future from the harvested wheat at an early stage before maturation of the wheat seeds. The invention relates to a method for estimating the end use qualities of a matured wheat seed, comprising measuring the expression level of at least 1 gene selected from genes, each of which is defined by any one of the nucleotide sequences of SEQ ID NOS: 1 to 121 in immature wheat.

2 Claims, No Drawings

SEQUENCE LISTING

```
<160> NUMBER OF SEQ ID NOS: 146

<210> SEQ ID NO 1
<211> LENGTH: 256
<212> TYPE: DNA
<213> ORGANISM: Triticum aestivum
<220> FEATURE:
<221> NAME/KEY: misc_feature
<222> LOCATION: (1...256)
<223> OTHER INFORMATION: n represents a, c, g or t

<400> SEQUENCE: 1
cgggtagcac actgggatat cctcaaggcc gagggcgatc tcnnnccttg ccaagattgg      60
```

```
gggcaaggtt atcaccnaga tcgggtcaag anccaatatt ggcnacaacg tgatcccctc    120
gggtttcaag attgnggcta aaggcaacan ctactgngtc tgggagaaga gtggcctctg    180
aattcatgct ggtgaatgga attagttcta gttttcaaan tatatattta ggactaaggc    240
atgatttatg aaatta                                                    256

<210> SEQ ID NO 2
<211> LENGTH: 194
<212> TYPE: DNA
<213> ORGANISM: Triticum aestivum
<220> FEATURE:
<221> NAME/KEY: misc_feature
<222> LOCATION: (1...194)
<223> OTHER INFORMATION: n represents a, c, g or t

<400> SEQUENCE: 2
cggctactgc ggtgcaggct gccacagngt acggctgcgt atggtgtctt cnccgaggcc    60
atcgncacca nctccnctct tctcggcana atgatgatnt tgntnntggt antcattgca    120
acgacgaaga atccgtggac anttccattg ccacgtncgg ttttcccttc acttactttt    180
actactagta ctta                                                      194

<210> SEQ ID NO 3
<211> LENGTH: 144
<212> TYPE: DNA
<213> ORGANISM: Triticum aestivum
<220> FEATURE:
<221> NAME/KEY: misc_feature
<222> LOCATION: (1...144)
<223> OTHER INFORMATION: n represents a, c, g or t

<400> SEQUENCE: 3
cggcgccatc accgccactc cactcttctc gcagaatgat gancgacctt cctatggnag    60
tattgcnacg acgaataatc cgtggcagtt tcattgccac gtacggtgtt cccttcactt    120
acttttagca ttagctagta ctta                                           144

<210> SEQ ID NO 4
<211> LENGTH: 195
<212> TYPE: DNA
<213> ORGANISM: Triticum aestivum
<220> FEATURE:
<221> NAME/KEY: misc_feature
<222> LOCATION: (1...195)
<223> OTHER INFORMATION: n represents a, c, g or t

<400> SEQUENCE: 4
cgggctattg ngntgcaggc tgccagagtg ggngctgcna tgncncnctt cnccgagagg    60
catnnccgcc aactccactc ttctccaaga atgntgatca atcntgntat ggcggtnttg    120
cnacgacgaa naatccgtgg gatctnattg ccaccgacgg tttcccttga cttactntta    180
gagtactagt cctta                                                     195

<210> SEQ ID NO 5
<211> LENGTH: 168
<212> TYPE: DNA
<213> ORGANISM: Triticum aestivum
<220> FEATURE:
<221> NAME/KEY: misc_feature
<222> LOCATION: (1...168)
<223> OTHER INFORMATION: n represents a, c, g or t

<400> SEQUENCE: 5
ccgggacggg agacgtttga agcttgaatg atcgngactg aaagngangg cgcgcgcatg    60
```
cagcattagt ggtaaagtnn gtantangta gcnntggaac aangnaatga gtcgttttc    120 ccctgtactc cctctgtaaa catatatnag agcgtttaga tcactact               168

<210> SEQ ID NO 6
<211> LENGTH: 165
<212> TYPE: DNA
<213> ORGANISM: Triticum aestivum

<400> SEQUENCE: 6
cggtgtggtt ctattcatcg gtcatgtggt caatccctc ctatcttcgt aatgtgtttg    60
ctctgaagtg tcttgtcatt tgcctcagct gttacatgta aggggagggt ttggacaatc   120
aatcatgcta cccatgcaat aaatccaata aatgttctat gctta                   165

<210> SEQ ID NO 7
<211> LENGTH: 129
<212> TYPE: DNA
<213> ORGANISM: Triticum aestivum
<220> FEATURE:
<221> NAME/KEY: misc_feature
<222> LOCATION: (1...129)
<223> OTHER INFORMATION: n represents a, c, g or t

<400> SEQUENCE: 7
cggggccaca catccacnac cnactctcgt cccccctcg caaaatctgg cgttggangc    60
tgccttgcca aancatgttt cccgttgcga gaaatnctgt aacaaatcca tcagtggtgt   120
acctagtta                                                          129

<210> SEQ ID NO 8
<211> LENGTH: 425
<212> TYPE: DNA
<213> ORGANISM: Triticum aestivum
<220> FEATURE:
<221> NAME/KEY: misc_feature
<222> LOCATION: (1...425)
<223> OTHER INFORMATION: n represents a, c, g or t

<400> SEQUENCE: 8
cggtctttcg accctgccag gcagaccgtt tcctacagcg gtgggttgag gcgctcacgg    60
atgctcgtgt aacccatgaa atccagggtc atctgggtct catactggtc acagtgcgac   120
gcatcccttg ggcagaagct ggcgtcgcgg ctcaagatga agccgaacat gtncatggac   180
aaggaggagg gaagcagtcg ctcacccgcc tcggttggcg tcggtcgagc caaggagggt   240
gcagcatgaa ctgaatctgt ctttgtgtgg gtgtagccat gaataaaaat gtgtaacagt   300
gaaatgaata tcgtatgtta taccgatgaa cgatgatggg gggtgttgtg atacaatgtt   360
gctgggttca tccgtcgtac cgtgtttgtg caaaagagan anntncaaga caatgtgttg   420
gttta                                                              425

<210> SEQ ID NO 9
<211> LENGTH: 433
<212> TYPE: DNA
<213> ORGANISM: Triticum aestivum
<220> FEATURE:
<221> NAME/KEY: misc_feature
<222> LOCATION: (1...433)
<223> OTHER INFORMATION: n represents a, c, g or t

<400> SEQUENCE: 9
cggtcncgtc tggacgtcac caagcgcgcc atcggcgtcg agatcaacaa gcaggttggc    60

| | |
|---|---:|
| nacaggatca tcaagaagag gatccatgtg cgtgtggagc acgtgcagcc atccaggtgc | 120 |
| aacgaggagt tcctccagag gaagctcaac aacgacaagc tgaaggcgga ggccaaggtg | 180 |
| cgtggtgagg tcatcagcac caagaggcag ccagcaggcc caagcctggg gttcatggtg | 240 |
| gagggcacca ccatcgagac ggtcaccccc atcccgtacg acgtcgtcaa cgatctcaag | 300 |
| ggtggttact agagcgcttg ttgtttcctg agcagaagct tgagccagtt cttagtatct | 360 |
| atgcttgttc ccaatgtttt ggtactgagt agttctcttt tgctccgcg gagtgtgaac | 420 |
| ttctctgtgg tta | 433 |

<210> SEQ ID NO 10
<211> LENGTH: 168
<212> TYPE: DNA
<213> ORGANISM: Triticum aestivum
<220> FEATURE:
<221> NAME/KEY: misc_feature
<222> LOCATION: (1...168)
<223> OTHER INFORMATION: n represents a, c, g or t

<400> SEQUENCE: 10

| | |
|---|---:|
| cggtagtccg tagctactct acggngagta gcgtcaggtc aagtcggaag ctgtggcttg | 60 |
| gtcaggtggc tggtctgcct ctgggcccag gagtgtctgc agtgtccact gtatccttgc | 120 |
| ttcttcagta atgtatgtcg tcttgctcaa atatgtcttg tctcgtta | 168 |

<210> SEQ ID NO 11
<211> LENGTH: 438
<212> TYPE: DNA
<213> ORGANISM: Triticum aestivum
<220> FEATURE:
<221> NAME/KEY: misc_feature
<222> LOCATION: (1...438)
<223> OTHER INFORMATION: n represents a, c, g or t

<400> SEQUENCE: 11

| | |
|---|---:|
| cggctcctgc tgcaagatgt ccactgtcca gacccgtgcg tatcattatt ctccctgtct | 60 |
| gtgccgcgca acagcagttt cctgnagccc tgcctccatc agcttctccc tcttccttgc | 120 |
| aatcggtgag ttcagcatac aagcttcaga ttgataagct cctatgtact gctgttctag | 180 |
| acaaacaatg acaacgacgc cttcttgttt ttagnactaa ccaacatttc agagaacaaa | 240 |
| gttattgctg taagtagctt tttgaaagtt ccttttcagn ctttcagtct tgggtacatg | 300 |
| aaaaaangat gtcncantct gaaanaattt ggccntgtat gtcaattcta gctgagaatt | 360 |
| actnatgatg atagcataat gagaggcntg cgtgcatgag tttacggant tacgccatga | 420 |
| cttntttccc ttcccttta | 438 |

<210> SEQ ID NO 12
<211> LENGTH: 134
<212> TYPE: DNA
<213> ORGANISM: Triticum aestivum
<220> FEATURE:
<221> NAME/KEY: misc_feature
<222> LOCATION: (1...134)
<223> OTHER INFORMATION: n represents a, c, g or t

<400> SEQUENCE: 12

| | |
|---|---:|
| cgggttcntc gcgcagctca tcgccgagat gaagagtgng tacaccgacn acttcttcnc | 60 |
| gcngattctc gggaagaatg ttcagcagct gtggaaggac tacnaagcca agtttagagg | 120 |
| ctgaacacac gtta | 134 |

<210> SEQ ID NO 13
<211> LENGTH: 201
<212> TYPE: DNA
<213> ORGANISM: Triticum aestivum
<220> FEATURE:
<221> NAME/KEY: misc_feature
<222> LOCATION: (1...201)
<223> OTHER INFORMATION: n represents a, c, g or t

<400> SEQUENCE: 13
cggccagntc ctcccccaa tggtggtacc atcgtcatag ctagatcgag gatggagaag      60
ctcgcgtaag aagagagtga agtgtgcccg tggtgtgtgg tctgtacgag caagtgtggc    120
gcgtcgagtc tcgagtgtca gctggtagta gttcggtagg ggcttttggc gctatancca    180
cttgngaagt gtcgagcgtt a                                               201

<210> SEQ ID NO 14
<211> LENGTH: 270
<212> TYPE: DNA
<213> ORGANISM: Triticum aestivum
<220> FEATURE:
<221> NAME/KEY: misc_feature
<222> LOCATION: (1...270)
<223> OTHER INFORMATION: n represents a, c, g or t

<400> SEQUENCE: 14
cggatgccca gggagatgca atgggacttc gtcagattac tcgtcgcccc ggggcagtgc     60
acttggcgac cattcacaat gttcgatact gccccgccgt ggaacagcct ctgtggatct    120
agagataaaa tcagtcgctc gtgaataagc atgcatgttg catccatagg cgtgtggtgt    180
gcatgnatac atatgtgagc tccgcgcgct caacatgtgt gggctatctg ctatgaatga    240
gaataaagag aatcattctg tggttctta                                      270

<210> SEQ ID NO 15
<211> LENGTH: 173
<212> TYPE: DNA
<213> ORGANISM: Triticum aestivum
<220> FEATURE:
<221> NAME/KEY: misc_feature
<222> LOCATION: (1...173)
<223> OTHER INFORMATION: n represents a, c, g or t

<400> SEQUENCE: 15 cgggangga gacgtttgaa agcttgaatg atcgagactg gananagaag gcgcgcgcat      60
gcagtnatta gtggtaaagt aagtannacg tagcngtgga acaaagtnat gagtcgtttt    120 tccctgtac tccctctgta aacatatatn agagcgttta gatcactact tta            173

<210> SEQ ID NO 16
<211> LENGTH: 92
<212> TYPE: DNA
<213> ORGANISM: Triticum aestivum
<220> FEATURE:
<221> NAME/KEY: misc_feature
<222> LOCATION: (1...92)
<223> OTHER INFORMATION: n represents a, c, g or t

<400> SEQUENCE: 16
cggtatgacg gnaactaggg cggcaagagt ggaacaaaac accaggcata aggccgagnc     60 ttccacccctt taccaagtnt atagatgcat ta                                  92

<210> SEQ ID NO 17
<211> LENGTH: 128
<212> TYPE: DNA

<213> ORGANISM: Triticum aestivum
<220> FEATURE:
<221> NAME/KEY: misc_feature
<222> LOCATION: (1...128)
<223> OTHER INFORMATION: n represents a, c, g or t

<400> SEQUENCE: 17

```
ggccaacaca tccaagaact actctcgtcc cccntnnca aaatctgtgc gttggangct        60
gccttgccaa atcatgtttc ccgttgcgag aaatgctgta acanatccnn cagtggtgta     120
cctagtta                                                              128
```

<210> SEQ ID NO 18
<211> LENGTH: 318
<212> TYPE: DNA
<213> ORGANISM: Triticum aestivum
<220> FEATURE:
<221> NAME/KEY: misc_feature
<222> LOCATION: (1...318)
<223> OTHER INFORMATION: n represents a, c, g or t

<400> SEQUENCE: 18

```
cgggaagatc gcccgggact tcangaccga cctccgcttc cagntcctcc gccgtctccg       60
cgctccaggg aggccgccgt aggcgtacct cgtcgggctg ttcgaggaca ccaacctgtg      120
ngccntccac gccaagcgcg ttaccatcat gcccaaggga catccagctc gcccgcngnn      180
tccntgngga gagggcctag gtttggggtc gctgctggct aanaactgtt cttgtcctat      240
gatctgaatg tgttcagggc gcttctgttt gttggngttg atatgatgta tcgtgatgct      300
tgaatgaaat tgcaatta                                                   318
```

<210> SEQ ID NO 19
<211> LENGTH: 263
<212> TYPE: DNA
<213> ORGANISM: Triticum aestivum
<220> FEATURE:
<221> NAME/KEY: misc_feature
<222> LOCATION: (1...263)
<223> OTHER INFORMATION: n represents a, c, g or t

<400> SEQUENCE: 19

```
cgggcgggcg aacaggaagg gccactgctc ctgcggcgcg gcctgcanct gcgcttcgtg       60
cggctcgncg accgcctgaa tcgatggccg acgcgtcnac gcgccactag tcgtgaacta     120
atgcactagn agtagagcta gctactgagt tagccatana taagtgccgc tgagccgtga     180
tgagtcatat gtgggcgcgt cgtgtgtatt acctacccac tcgcatcagt gtgtaagaac     240
gaataaatag tttctgtgag tta                                             263
```

<210> SEQ ID NO 20
<211> LENGTH: 62
<212> TYPE: DNA
<213> ORGANISM: Triticum aestivum

<400> SEQUENCE: 20

```
cggtctgtgc tagttcagct tggggatgaa agacaaacaa agttcttggt ttgccagcat       60
ta                                                                     62
```

<210> SEQ ID NO 21
<211> LENGTH: 347
<212> TYPE: DNA
<213> ORGANISM: Triticum aestivum
<220> FEATURE:
<221> NAME/KEY: misc_feature

```
<222> LOCATION: (1...347)
<223> OTHER INFORMATION: n represents a, c, g or t

<400> SEQUENCE: 21
cggcgacngg ggcgccncat cacgggcgag gatcgtcnac cantgcgccn acggcgggct    60
ggaacctgga ctgggacacc gtcttcacca agatcgacnc caacgggatc gggtaccagc   120
agggccacct caacgtcnac taccagttcg tcgactgccg cgactagatt atgtatccgt   180
cgatcaaagg ctagcttgct atgataagaa taagaggcta gcttagctac gagtgagctc   240
agactggtcg atgctgttga ataaaagcta gcacgtgatg ctgcattgta tacgtgtata   300
caatacgtac atggaatgaa ataaagtgga tcaaatcata cgggtta                 347

<210> SEQ ID NO 22
<211> LENGTH: 259
<212> TYPE: DNA
<213> ORGANISM: Triticum aestivum
<220> FEATURE:
<221> NAME/KEY: misc_feature
<222> LOCATION: (1...259)
<223> OTHER INFORMATION: n represents a, c, g or t

<400> SEQUENCE: 22
cggacacntc atgacnccct cttnnctgat caggcncgta gatcctgtng catnatggnt    60
gcngacncca ccatgggtca gtgngcaata aanttgacgc cnacccgaac gggcgtctcg   120
tgtctgctga atgattcnta tactntcatg ttcggcnnga gaggcgaggc gaggcttatc   180
aggnntngca cttctatccg tgcngcnntt ntcngatgat gaagttacna tgtcacccag   240
ccggtatttn cttgaatta                                                259

<210> SEQ ID NO 23
<211> LENGTH: 174
<212> TYPE: DNA
<213> ORGANISM: Triticum aestivum
<220> FEATURE:
<221> NAME/KEY: misc_feature
<222> LOCATION: (1...174)
<223> OTHER INFORMATION: n represents a, c, g or t

<400> SEQUENCE: 23
cgggaanggg aggcgtttgn aagcttgaat gatcgagact gaanagagaa ggcgcgcgca    60
tgcagtcatt agtggtaaag taagtagtan gtagcantgg ancaaagtaa tgagtcgttt   120
ttcccctgta ctccctctgt aaacatatat nagagcgttt agatcactac ttta         174

<210> SEQ ID NO 24
<211> LENGTH: 251
<212> TYPE: DNA
<213> ORGANISM: Triticum aestivum
<220> FEATURE:
<221> NAME/KEY: misc_feature
<222> LOCATION: (1...251)
<223> OTHER INFORMATION: n represents a, c, g or t

<400> SEQUENCE: 24
cggtgcaagt gcatcaggca gtgctgatca tatgtgctac ggctagctgg ccttcgccgt    60
acntcancta gcttgcccat ggnaaccata cgctctgtgt acctacttga ntgncngngc   120
ccctttctac gtacgtatgt cgtatgtatg tccgtgtcat cactagccag ccagctgctg   180
catctcgatc gatgcatgca tgggcgggct aaggtataat aataagaata aaacgtacgg   240
ttcangtttt a                                                        251
```

<210> SEQ ID NO 25
<211> LENGTH: 237
<212> TYPE: DNA
<213> ORGANISM: Triticum aestivum
<220> FEATURE:
<221> NAME/KEY: misc_feature
<222> LOCATION: (1...237)
<223> OTHER INFORMATION: n represents a, c, g or t

<400> SEQUENCE: 25

```
cggcgncttc tctgnaagcn tctggggcgc nngtctgggt ccnngtagct actgntcttg      60
agtangntan cgngcagngc ctcaaagcta tgtaggctgc tcttatngnt nttactctgt     120
aacatnatag tgctgtgccc gatnnntgtn nntcancgng ancccntgtt gnagaagatn     180
catgcgctgc nccangtgca gaaagtactg taaangantn actggcgncn gacatta       237
```

<210> SEQ ID NO 26
<211> LENGTH: 223
<212> TYPE: DNA
<213> ORGANISM: Triticum aestivum
<220> FEATURE:
<221> NAME/KEY: misc_feature
<222> LOCATION: (1...223)
<223> OTHER INFORMATION: n represents a, c, g or t

<400> SEQUENCE: 26

```
cgggatggcc tacttcatcg tcgccgacag accatcctct ccatggccag gaagcactcg      60
cacgagatgg cgccngagca cctggaagaa cacctccttc cactanttag cctatagtag     120
atccattatt agtatagtgt gtaataaacc gtgtctgctg aagcctgaaa gatggtataa     180
tgttgagcga gaggggcgat caggcgaggt gatggtataa tta                      223
```

<210> SEQ ID NO 27
<211> LENGTH: 266
<212> TYPE: DNA
<213> ORGANISM: Triticum aestivum
<220> FEATURE:
<221> NAME/KEY: misc_feature
<222> LOCATION: (1...266)
<223> OTHER INFORMATION: n represents a, c, g or t

<400> SEQUENCE: 27

```
cctacttcat cggtcgccga cagaccatcc tctccatggc caggaggcac tccttcgacg      60
acgcgccaga gcacctcagg aacacctcct tccactaatt agactataat agtagacacn     120
tatnatgttc tataatggta ctataatgtt cagcgagagg ggcggncagg cgaggtgatg     180
gtataattat ctgatgatgt atgtatgtaa taatgtggcc atgttctttc cagggatctt     240
gtcatctttc cnggqatcgt gaatta                                          266
```

<210> SEQ ID NO 28
<211> LENGTH: 108
<212> TYPE: DNA
<213> ORGANISM: Triticum aestivum
<220> FEATURE:
<221> NAME/KEY: misc_feature
<222> LOCATION: (1...108)
<223> OTHER INFORMATION: n represents a, c, g or t

<400> SEQUENCE: 28

```
ccggcatcta gaccgtacta atgggncacc ctaccgtatg ttgcacgtat acctgaactn      60
cnacagttnt atnattggga tgtgctcatg caactgtctg tattgtta                 108
```

```
<210> SEQ ID NO 29
<211> LENGTH: 159
<212> TYPE: DNA
<213> ORGANISM: Triticum aestivum
<220> FEATURE:
<221> NAME/KEY: misc_feature
<222> LOCATION: (1...159)
<223> OTHER INFORMATION: n represents a, c, g or t

<400> SEQUENCE: 29
cggatgnctc tcgagtgagc ntgggtcgag cgatcgcgtc cgaatacacc gccgatggat      60
ttgaggttac cacnggattt angtatgcgt atcttctntg gtggaccagg gtccaagagg     120
gcctgatgat agtaatctat gtatgggctc gacaagtta                            159

<210> SEQ ID NO 30
<211> LENGTH: 208
<212> TYPE: DNA
<213> ORGANISM: Triticum aestivum
<220> FEATURE:
<221> NAME/KEY: misc_feature
<222> LOCATION: (1...208)
<223> OTHER INFORMATION: n represents a, c, g or t

<400> SEQUENCE: 30
cggccttctc gttccngtgt cctctctgtg cangcatgcg agtgagagaa agaccaccat      60
gttttcactc ttcaattatt actccttgtc accgttactg ttgtcgaatt acattantta    120
ctactgttat tagtgttggt gttggatgga tgatgaacct gtaatgtaaa accgctgtga    180
ntgagaattg ctgcaatttg gaacgtta                                       208

<210> SEQ ID NO 31
<211> LENGTH: 79
<212> TYPE: DNA
<213> ORGANISM: Triticum aestivum

<400> SEQUENCE: 31
cggtatacgt acgagagccc gtttgcactt tgcacagtga tcttggagaa cacacccctc      60
tgtgttcttg tatgtatta                                                  79

<210> SEQ ID NO 32
<211> LENGTH: 64
<212> TYPE: DNA
<213> ORGANISM: Triticum aestivum
<220> FEATURE:
<221> NAME/KEY: misc_feature
<222> LOCATION: (1...64)
<223> OTHER INFORMATION: n represents a, c, g or t

<400> SEQUENCE: 32
cgggtgggcc aggntccaga ctcgtttgag gttgttgagg ctngnggngt gtcaacnggc      60
ctta                                                                  64

<210> SEQ ID NO 33
<211> LENGTH: 188
<212> TYPE: DNA
<213> ORGANISM: Triticum aestivum
<220> FEATURE:
<221> NAME/KEY: misc_feature
<222> LOCATION: (1...188)
<223> OTHER INFORMATION: n represents a, c, g or t

<400> SEQUENCE: 33
cggtagcccc ctgtncccn ccgagntngc agngcnccaa taaggccgtn gcctcttggc       60
```

-continued cgtgccgcct atgccngact gnactgctgg gnannttctg cnatcagcat gattcanccc    120
ganggccgga tcnaagtcct gtgncagnng ctgactatgg atctcangta ntggnaagnc    180
ttgcgtta                                                              188

<210> SEQ ID NO 34
<211> LENGTH: 172
<212> TYPE: DNA
<213> ORGANISM: Triticum aestivum

<400> SEQUENCE: 34
cggagtcctt cgccgtagct taccagtaac caccgcatga caaataagat cccccccttc    60
tgggtgttgg tgtacaaatc ccgtgtgctc tgcttctctg tactctttta tcagtggaac    120
atgcatagat ttcactgagc atgtatggtc tcttctgcac tgaacatggt ta            172

<210> SEQ ID NO 35
<211> LENGTH: 199
<212> TYPE: DNA
<213> ORGANISM: Triticum aestivum
<220> FEATURE:
<221> NAME/KEY: misc_feature
<222> LOCATION: (1...199)
<223> OTHER INFORMATION: n represents a, c, g or t

<400> SEQUENCE: 35
cgggtgnaca ttgacccagg gatgtatgaa tccgtcgaag gtgagggcac caacgnaagn    60
aggccctcac gcgcttcgcc agggaagctc tctgaggagc gcaagctgcg ccaaaccaac    120
ctcaactcca aatagagaag aggacgattt gagcgaaaga gaagagagac gaagaagcac    180
tagctagctg ctatgctta                                                  199

<210> SEQ ID NO 36
<211> LENGTH: 220
<212> TYPE: DNA
<213> ORGANISM: Triticum aestivum
<220> FEATURE:
<221> NAME/KEY: misc_feature
<222> LOCATION: (1...220)
<223> OTHER INFORMATION: n represents a, c, g or t

<400> SEQUENCE: 36
cggcaagtga ggcgttggcg ctcgctagct gcgagttgta gccntatatc aaggcactgc    60
ggtggactgc acacatnatg ggtggttcag nttgtancat catggtgtaa attacaagga    120
tctttgggga aatggtttga tctgcccgct tgcttcatgt cctggatgta gcctgtgtgt    180
tgctccatga gaaatgagaa cnatgaaaac ttggncgtta                          220

<210> SEQ ID NO 37
<211> LENGTH: 243
<212> TYPE: DNA
<213> ORGANISM: Triticum aestivum
<220> FEATURE:
<221> NAME/KEY: misc_feature
<222> LOCATION: (1...243)
<223> OTHER INFORMATION: n represents a, c, g or t

<400> SEQUENCE: 37
cgggtnttgg nctccagttg gatgcttcag agctcaccta ctttacnggg cacaggtacg    60
acgttgaagt tccggattca tatgagnatc ttcttttgga tgttctngat ggcgatagtc    120
atctcttcat gcgcantgac naattagctg ctgcatggag cgtattggca cctatactcc    180
atgagatcga ccngaagagt gttgctcctg anctctacga cgctggggat aaaggaccaa    240
tta                                                                      243

<210> SEQ ID NO 38
<211> LENGTH: 420
<212> TYPE: DNA
<213> ORGANISM: Triticum aestivum
<220> FEATURE:
<221> NAME/KEY: misc_feature
<222> LOCATION: (1...420)
<223> OTHER INFORMATION: n represents a, c, g or t

<400> SEQUENCE: 38
cggaggcggg catcaagang ggacagatga aggtagttat gctgatagtg gacatggtat     60
gaagaatgat gttccgtatg aggantctgt gcatgatant gatgaaaatg atgctgatga    120
taaggcggaa ggtccaccct cttctaatga tgatggcaca tcagcnagcg ttggaggcca    180
acagaacgaa aagactgaca atcctaaaaa caacaaaaag aacaagaaag gcgcagagaa    240
gaaaacaact gtttctgctg acctaaagat cacatcanag ggaaagaagc aaaaggaggt    300
ttcganggca cgcaatgatt gtgaaacatg tggagatact ttcgagtcaa ggagcangtt    360
gttttctcat ttggaagaaa caggtcatgc tgtgatcaag gcacgacnga aaagcgtta     420

<210> SEQ ID NO 39
<211> LENGTH: 355
<212> TYPE: DNA
<213> ORGANISM: Triticum aestivum
<220> FEATURE:
<221> NAME/KEY: misc_feature
<222> LOCATION: (1...355)
<223> OTHER INFORMATION: n represents a, c, g or t

<400> SEQUENCE: 39
cgggcccngt acccgtcgcc ctacgcgacg taccccgccc acgcgcccca gtatgttcag     60
cgacgnagaa ccccaacgcc tgctccgtca tgtgagctgc catgccacgc cacgccacga    120
gccgatgagc acgacgccaa gnccagagtc gccgcaagnn gtatgaatca aaccaganaa    180
gcacggcctg ggtttggcgc gcggtaccat tagcctagct agcagctggt agttacgtag    240
cttagcgcac cgagaattag cagacntgta cntggcgacn gcgatcccgt cccgcgatgt    300
antgtaatgt aatgttccac gatccatccg ataaattttg gccctgcact cgtta          355

<210> SEQ ID NO 40
<211> LENGTH: 176
<212> TYPE: DNA
<213> ORGANISM: Triticum aestivum
<220> FEATURE:
<221> NAME/KEY: misc_feature
<222> LOCATION: (1...176)
<223> OTHER INFORMATION: n represents a, c, g or t

<400> SEQUENCE: 40
cggggtaaca aggacgacnt cgcttgcgtt gtcntgcgca tccnttgacc tgcancgatg     60
catatacgat catgtgtttg ttctgtggtg cgtagaacca gttttgtanaa gggaggtgag   120
ctgaagtgtt tgctgtgaac ttacagaaag ganatgcact ggactgtttg atgtta        176

<210> SEQ ID NO 41
<211> LENGTH: 128
<212> TYPE: DNA
<213> ORGANISM: Triticum aestivum
<220> FEATURE:
<221> NAME/KEY: misc_feature
<222> LOCATION: (1...128)

<223> OTHER INFORMATION: n represents a, c, g or t

<400> SEQUENCE: 41

```
cggtanccca tggggtcgt cggnaggccg acgcacgaac cagtctcctc angtagcttc      60
ctggncgnag gtcagcgagg ccgaagcgcg acnacgaagt cctcaggaat acttggttgc    120
ttcaatta                                                              128
```

<210> SEQ ID NO 42
<211> LENGTH: 219
<212> TYPE: DNA
<213> ORGANISM: Triticum aestivum
<220> FEATURE:
<221> NAME/KEY: misc_feature
<222> LOCATION: (1...219)
<223> OTHER INFORMATION: n represents a, c, g or t

<400> SEQUENCE: 42

```
cgggacggat ctaagatgat cangagcctg tccctaggg tggtgactct tgttgagcag       60
gagtcgaaca cnaacacaag tgcattcttg ccaaggtact tggagaccct cgactactat    120
acggcaatgt ttgagtcaat agangttgct ctnccaaggg atgataagag gcggattagc    180
acggagcatc actgtgtngc aagggatatc gtcaattta                            219
```

<210> SEQ ID NO 43
<211> LENGTH: 284
<212> TYPE: DNA
<213> ORGANISM: Triticum aestivum
<220> FEATURE:
<221> NAME/KEY: misc_feature
<222> LOCATION: (1...284)
<223> OTHER INFORMATION: n represents a, c, g or t

<400> SEQUENCE: 43

```
cgggangtcg tcctctccac gccncgcctc gagagcaagn gcctcgngct cgcgctcaag      60
gaaggnaatt cnacacgaca tacgggnctg cttggcactg catcgtcggc acaagctttg    120
gctcctacgt nactcactcc ntangaggct tccngtactt ctcggtcgac aaggcgtana    180
ttcttctctt cagaaccgct gtcgagccac tgagnanacc gtgatgaggc ctggaaccta    240
tcttctcaca cacaagtgta gatttagcgc gtatgtgtaa ttta                      284
```

<210> SEQ ID NO 44
<211> LENGTH: 300
<212> TYPE: DNA
<213> ORGANISM: Triticum aestivum
<220> FEATURE:
<221> NAME/KEY: misc_feature
<222> LOCATION: (1...300)
<223> OTHER INFORMATION: n represents a, c, g or t

<400> SEQUENCE: 44

```
cggtatcggt gccnccnct cgntcgaggg tncattcctc tcgagtgagc atatggtcag       60
gaaaattgtc tttggtgtct ggaatccagt tgttcttatc gttgtcnaat gtagcgcctg    120
atataccgac tgtcngtctn ttggnggagc agcacccntt gaaccctgaa ctaatcctgt    180
tccagatttt gttccagatt tgaagttat cgtanggaag gtcgaacatg tttatctcct    240
ttggcagttg tcanatgttc tgatttgtgt gctcttctaa attttgatca gattgctta    300
```

<210> SEQ ID NO 45
<211> LENGTH: 260
<212> TYPE: DNA
<213> ORGANISM: Triticum aestivum

```
<220> FEATURE:
<221> NAME/KEY: misc_feature
<222> LOCATION: (1...260)
<223> OTHER INFORMATION: n represents a, c, g or t

<400> SEQUENCE: 45
cggaatgggc ggctactgat aagatgagag ctctagctat ccnannaatg gaccaccant      60
gtttagtcga tggctccgat ccctatgtag cggtganaaa taaagtgcca tgcattatca     120
tgtgtggact agtactggcn ctagattcaa acttgggaat aaanggcaaa ctaagttatt     180
ttctgcatat agcgttatcc gcgtgtttcc attcgggcac acgtggatat gtncnttcct     240
naccacaatn ttatgcatta                                                 260

<210> SEQ ID NO 46
<211> LENGTH: 120
<212> TYPE: DNA
<213> ORGANISM: Triticum aestivum
<220> FEATURE:
<221> NAME/KEY: misc_feature
<222> LOCATION: (1...120)
<223> OTHER INFORMATION: n represents a, c, g or t

<400> SEQUENCE: 46
cggaacgagc agagcgtgcc gccgcttccc ttgaaagtag tggtcacgct gngcaaatca      60
atcttgtttg tccgtattgt aactgctaat aatagttctg atgagctaat aaggccatta    120

<210> SEQ ID NO 47
<211> LENGTH: 190
<212> TYPE: DNA
<213> ORGANISM: Triticum aestivum
<220> FEATURE:
<221> NAME/KEY: misc_feature
<222> LOCATION: (1...190)
<223> OTHER INFORMATION: n represents a, c, g or t

<400> SEQUENCE: 47
cggggttcct gtggaggcga tgctgctgca cgccgctacc naggtgattc gaaagancaa      60
atgnaaagac acatggccnt atntattcan taaagtgcat gaantgcaac ctnttatatt    120
tccntatcca catgatcacc tanatanacg taggtgtnag aaatgtgaac atgtggtgtg    180
agagtggtta                                                            190

<210> SEQ ID NO 48
<211> LENGTH: 278
<212> TYPE: DNA
<213> ORGANISM: Triticum aestivum
<220> FEATURE:
<221> NAME/KEY: misc_feature
<222> LOCATION: (1...278)
<223> OTHER INFORMATION: n represents a, c, g or t

<400> SEQUENCE: 48
cgggcccaga tcgagangtg gactnagtga gtcgtgacag gtccctggca gtggtactgt      60
gttcggtcgc ctgtggncnt gtggctctgt cgaataacgc aggatgcttg tatgantgta    120
gttttttcga gggaatgatg tacacctagg ttagctagag gatatgataa ataatgtgta    180
aacgcangan cgacatacac atgtggntct tgtagtatgt tgtttttgct tganttcagg    240
anatgagaaa tatattacca gttcgttgtc cttgatta                             278

<210> SEQ ID NO 49
<211> LENGTH: 203
<212> TYPE: DNA
```

<213> ORGANISM: Triticum aestivum

<400> SEQUENCE: 49

```
cggtagtgtc cggacagtac acgttcgggt cgattgagtg gagcgacggc gagcactcgg      60
tgacgagccc catcgccatc acctggccga cgagcaaggt tgcggagatg tgaatgtgat     120
cgccgtgggg tgtgtacaac atagtacgtg cgattatgcg agaatttatc tcatttgctg     180
taagtttcac ttcctatcag tta                                             203
```

<210> SEQ ID NO 50
<211> LENGTH: 281
<212> TYPE: DNA
<213> ORGANISM: Triticum aestivum
<220> FEATURE:
<221> NAME/KEY: misc_feature
<222> LOCATION: (1...281)
<223> OTHER INFORMATION: n represents a, c, g or t

<400> SEQUENCE: 50

```
cggctggatc ggggtgggtc ggccgcagct acctcatcgc cgtcagcggc gagaagaagc      60
ccgccatgtn gggaagatca tcatcgacgt cgagctcgcc gccagggatc atccccaggg     120
gcttcatctg gcccgtcgcc gcctaccgcg agctcatcaa cggcgacctc gtcgtcgacg     180
acgccgacnt cggctactaa tcagctgcca tgcgtgcgtg gttggctagt cagtcccaac     240
tcagatggac agcggaggat ggatgacttg ttgngtcgac c                         281
```

<210> SEQ ID NO 51
<211> LENGTH: 117
<212> TYPE: DNA
<213> ORGANISM: Triticum aestivum
<220> FEATURE:
<221> NAME/KEY: misc_feature
<222> LOCATION: (1...117)
<223> OTHER INFORMATION: n represents a, c, g or t

<400> SEQUENCE: 51

```
cggaaagggt ggtagaagag gatngaggct gngattccat gctcgntcna ggatggaaca      60
ntaccnggct atcggatctc ctgcgncttg nnacttgtct ctgtactact ccgttta        117
```

<210> SEQ ID NO 52
<211> LENGTH: 274
<212> TYPE: DNA
<213> ORGANISM: Triticum aestivum
<220> FEATURE:
<221> NAME/KEY: misc_feature
<222> LOCATION: (1...274)
<223> OTHER INFORMATION: n represents a, c, g or t

<400> SEQUENCE: 52

```
cgggcccaga tcgagaagtg gactagtgag tcgtgacagg ncctggagt ggtactgtgt       60
tcggtcgcct gtggtcntgt ggctctgtcg aataacgagg atgcttgtat gagtgtagtt    120
ttttcgaggg aatgatgtac aactaggtta gnagaggata tgataaataa tgtgtaaacg    180
caagaacgac atacacatgt ggntcttgta gtatgttgtt tttgcttgag ttcaggagat    240
gagaaatata ttaccagttc gttgtccttg atta                                274
```

<210> SEQ ID NO 53
<211> LENGTH: 172
<212> TYPE: DNA
<213> ORGANISM: Triticum aestivum
<220> FEATURE:
<221> NAME/KEY: misc_feature

```
<222> LOCATION: (1...172)
<223> OTHER INFORMATION: n represents a, c, g or t

<400> SEQUENCE: 53
cggctncagg actncagatc actccgatgc ttgnatatcg gtccatcatt gtngtctacc     60
cttgnatgtg tgcctgccna ngcagacgta aataagatcn ntangcagca tgtatggatt   120
ggngtggttc atgctgtcga tcgaataang tcttgcactn nntgactatt ta           172

<210> SEQ ID NO 54
<211> LENGTH: 116
<212> TYPE: DNA
<213> ORGANISM: Triticum aestivum

<400> SEQUENCE: 54
cggacggagg gagtactacc atatgtaact ttgatcattg gacctgctta tgacgcgcat    60
gcatgtgtag tcctgcttcg ctctgctatc gtagagatgg aaatcaatca atatta       116

<210> SEQ ID NO 55
<211> LENGTH: 319
<212> TYPE: DNA
<213> ORGANISM: Triticum aestivum
<220> FEATURE:
<221> NAME/KEY: misc_feature
<222> LOCATION: (1...319)
<223> OTHER INFORMATION: n represents a, c, g or t

<400> SEQUENCE: 55
cggggagatt gctagantca gtttcagaaa aagatatgct tgccttgaca agagancaaa    60
ngagatgcag tgatctcttg acatacctct atttgagatc agangaaaat acagtgcagt   120
ttcagttatt gcctggaaaa ttcttttgct atcaactgct acctgaaatt gtgagctaca   180
tatagtttag cttttgtttg ttgggtgttg ccactcttca gaagcaccga ggcagaatan   240
aataagccca tgaacattcc tttgctccag cantcagata tagaaggcta atctgagagg   300
aatttcaaat ttgtaatta                                                319

<210> SEQ ID NO 56
<211> LENGTH: 234
<212> TYPE: DNA
<213> ORGANISM: Triticum aestivum
<220> FEATURE:
<221> NAME/KEY: misc_feature
<222> LOCATION: (1...234)
<223> OTHER INFORMATION: n represents a, c, g or t

<400> SEQUENCE: 56
cggcgacatc agggagactt tgggttgccn ccacccgcgg agctacctca aagtttgact    60
agcttgaact tagataccat agtttaccct gcaactgtac attgggtatg ttgtctcttg   120
ngctgnngtn ctgttgnatn cctgtctccn acaatgtgct gctccatggt gnaccgnnag   180
gctgctgctc naggaagagt cccccacat ctgaattacc ngtttcngac ttta          234

<210> SEQ ID NO 57
<211> LENGTH: 425
<212> TYPE: DNA
<213> ORGANISM: Triticum aestivum

<400> SEQUENCE: 57
cgggcgcctc tgcttcgggg gcggcgaagc cgctccgcgg cgtctcactg tggcggcggc    60
ggcgtcctcg tcttcgtcgg gccctctcta cccgacgcct ccccccaccg agcagacaat   120
```

```
tgagcgcgcc aagctcgagc aggttatcaa gaggctagag aaaacagcta ggtatttcaa    180
gaatttgggt accctagggt tctggtccca gttggtgtgc acgtttgttt ctgctggaat    240
tttgtcattc tccacagttg ttactgggaa ggttacatca cccttttacat tctacacaac   300 tgctgctggc gttgctgcag cttttatttc agtcttctgg tcatttggct acatccgtct    360
ttctgaaaga cttcggaaaa cagcaagtgc acccgcaaag gctcctccac gggctgatgt    420
gatta                                                                425
```

<210> SEQ ID NO 58
<211> LENGTH: 301
<212> TYPE: DNA
<213> ORGANISM: Triticum aestivum
<220> FEATURE:
<221> NAME/KEY: misc_feature
<222> LOCATION: (1...301)
<223> OTHER INFORMATION: n represents a, c, g or t

<400> SEQUENCE: 58

```
cggagtggct gtcgttggtc ttttcgggat gaacattggt atatcacttt acaccccgt      60 aggtgaggta gcanacgcga gcagcgcatg tgaagttttg ggaaaccact ttcggcacca    120 tgctgggtg cacgatcctg tacgtaatag ccatggggttg ggggaagaga agtgggctat    180
tgcaatgagg gtgcacccaa tcctgtcaac aactgctccc gcagaagcct tcgctggaca    240 accctaaaa gagggcggca cgcgcctgga ttgtatttgt acctgaaaat gcataccttt     300
a                                                                    301
```

<210> SEQ ID NO 59
<211> LENGTH: 412
<212> TYPE: DNA
<213> ORGANISM: Triticum aestivum
<220> FEATURE:
<221> NAME/KEY: misc_feature
<222> LOCATION: (1...412)
<223> OTHER INFORMATION: n represents a, c, g or t

<400> SEQUENCE: 59

```
cggggannac ctggcctgct tctgggcgcc tgaccacnag ccgcccgtca ccgtcacctt     60
cnagttcgac tggnngacgg cgtcatggcc aaggactggt ccaacgtcgc cgagaagggc   120
naggtcnata tgatggaact agagctgacg angctagagg ataccatcaa atctatccnt   180
gaagaaatgt tttatctacg tgaangggag gaggaaatgc anaacatcaa caggccgaca   240
agctcgagga tggggtggct gagtttcctc tcgctcggca tctgcttatc cgnggcnggn   300
ctgcanctgt ggcatctgaa naccttttttc gagagaaaga agctgctgta gttccccat   360 gatcacaaac aaatcgttgn gaattagggt atattgtttc tgccagctgt ta            412
```

<210> SEQ ID NO 60
<211> LENGTH: 431
<212> TYPE: DNA
<213> ORGANISM: Triticum aestivum
<220> FEATURE:
<221> NAME/KEY: misc_feature
<222> LOCATION: (1...431)
<223> OTHER INFORMATION: n represents a, c, g or t

<400> SEQUENCE: 60

```
cgggggggtng cctttgttga ctttcagaac ntgancntgc tcttgtagct ctgagggttc     60
tanacaacag ccctggancc tttggtacag naacggcgtc canttgtcga gtttgcactt   120
gaggatgttg aannntgagg ctccnnaaga ttcnnaacga ncgcnatggt agggcaaaag   180
```

```
aggctgcaca agagcgaagg gctctgggag atcagnctac aactgatggc cctcnttcnn    240
ataagnaana naccttttgg aaaagggagc acgcnagant cgcnggatat accatcnnaa    300
ttatcngact ctggcaaagg accttcagat gatctgtcag ttcctggagg tcctaanacc    360
actgtgngaa agcacacang gagacaaanag gcatctcan angcccgcna ancgagcacg    420
gnagtcaatt a                                                         431
```

<210> SEQ ID NO 61
<211> LENGTH: 161
<212> TYPE: DNA
<213> ORGANISM: Triticum aestivum
<220> FEATURE:
<221> NAME/KEY: misc_feature
<222> LOCATION: (1...161)
<223> OTHER INFORMATION: n represents a, c, g or t

<400> SEQUENCE: 61

```
cgggangaac tggcgaggna agtcgcggta tttagcgtcg cagatcgagg aacatgtnag     60
aangnaggaa ggacanggtg ctggtaacag tacctcacgc tcaaggagac gaacangcag    120
ctgatacaac aggcncatca tctatcgctt tcnttccttt a                        161
```

<210> SEQ ID NO 62
<211> LENGTH: 367
<212> TYPE: DNA
<213> ORGANISM: Triticum aestivum
<220> FEATURE:
<221> NAME/KEY: misc_feature
<222> LOCATION: (1...367)
<223> OTHER INFORMATION: n represents a, c, g or t

<400> SEQUENCE: 62

```
cggtgagcca ganagatgaa tgatggcaag gggtctcaca aaagcagaca ccccgccgc      60 caccaccatc accatcatga tcaccatgcc aactctgctg aacccagtga cgggaagcaa    120
ctcgtgtaag ttgctaatgc ctcanaacct gattggcatc ttcactggac tctgtgacgg    180
caatgtttgc ttgccccagt tggccagttg ctgaatgaag gcgatgtatc tttcataatg    240
ttactgtctc ggctctgctg cggctttctg aagcctgtac ttgttgtacc gaaacatttg    300
gcgaaaccag atgttatttc cagcgtttcc tctgttgtca tatgtttgct tgctgatttg    360
gtggtta                                                              367
```

<210> SEQ ID NO 63
<211> LENGTH: 257
<212> TYPE: DNA
<213> ORGANISM: Triticum aestivum

<400> SEQUENCE: 63

```
cggccagggt acgacgccta caactggggc aacttcttca gcaccaggaa gaacagcaac     60
ttcagggaag ctcgacgtcg aaaacgtcca gatcgcacac ttcagaaagg accgatcttg    120
aatgaaggat ccatcgtgaa ttcatgatcc taccgctctc ctcggtgatc ctaatgctac    180
aagcatctcc ccgtttgtag taatataaat aagtaattgt gtcggttcaa aaataaata    240 agtaattgtc cgtatta                                                   257
```

<210> SEQ ID NO 64
<211> LENGTH: 267
<212> TYPE: DNA
<213> ORGANISM: Triticum aestivum
<220> FEATURE:

```
<221> NAME/KEY: misc_feature
<222> LOCATION: (1...267)
<223> OTHER INFORMATION: n represents a, c, g or t

<400> SEQUENCE: 64
cggagggtgg gncgtgaaag ngcntctntg agctcatcta ggaggcncat ctgcgnngtg      60
tatccncatc ttcctcaaga tcntcntccg agaacgncnt cnnctacncc gacnnctncc    120
gccnnaagac cgtcaccgcn atggacntcg tcnnggnngt cnagtnccnn gtccggnccc    180
tggacngctt cctctactga ntaggcgngt gantggctgg ncctggctgc actntgnatg    240
actctgntgn tncatgntng nctntnt                                        267

<210> SEQ ID NO 65
<211> LENGTH: 129
<212> TYPE: DNA
<213> ORGANISM: Triticum aestivum
<220> FEATURE:
<221> NAME/KEY: misc_feature
<222> LOCATION: (1...129)
<223> OTHER INFORMATION: n represents a, c, g or t

<400> SEQUENCE: 65
cggaagacta cttcgattta cttggtttgg acctgaggan gangaatgga ttgatgtttg     60
tnaaggtgtg agactgcntt ctcntcanng tgtcgctgtg ctgcctgggn ancccatgtc    120 ttngtatta                                                            129

<210> SEQ ID NO 66
<211> LENGTH: 388
<212> TYPE: DNA
<213> ORGANISM: Triticum aestivum

<400> SEQUENCE: 66
cggggcctaa ggcgctgaac tggacccagg gccccagggc gacctgaagc catggtaggt     60
agcggcggcg gcattggcac catgagctga cgatgttcag tcagaatgaa atgagaggac    120
tgatgagtaa gccaagccaa gccaagccat tactgtcatc aaatgtaaag ctccttcctg    180
tctaataccc accttgcttct ttttgttgtg atgatgtgcc tgcctacctt ccatgttgtg    240
gcatggcatg gttcccttgt tttttgttgc cctagtgctt agaactgctg ctgttgtagg    300
tgatcatgga tcatagtgtt atatatattg catgaccttt gtattatact gctacataga    360
cgccgatctg taatggcggg aataatta                                       388

<210> SEQ ID NO 67
<211> LENGTH: 303
<212> TYPE: DNA
<213> ORGANISM: Triticum aestivum
<220> FEATURE:
<221> NAME/KEY: misc_feature
<222> LOCATION: (1...303)
<223> OTHER INFORMATION: n represents a, c, g or t

<400> SEQUENCE: 67
cgggatatgc atcctctgaa tccaaccgat ggatganctt gcatgctttc cangcntttg     60
gtgcccattc tttctgttct tcttgcttgt ctccttctcg nggcaaagag ggcaggggat    120
tgagaggggt agcatcgatc gattgattca ttttgtgaaa tcatttcacn ctagatgatt    180
attacccaag ttantacact atatatgtcc acaaacatac acagagtagt antactccag    240
tatgcntgca ncacatgcat gcatgtatgc tggtcctggc cgactctcgg nggcctgtaa    300
tta                                                                  303
```

<210> SEQ ID NO 68
<211> LENGTH: 106
<212> TYPE: DNA
<213> ORGANISM: Triticum aestivum
<220> FEATURE:
<221> NAME/KEY: misc_feature
<222> LOCATION: (1...106)
<223> OTHER INFORMATION: n represents a, c, g or t

<400> SEQUENCE: 68
cggctgccaa tactggtagc caggattttc acctgatctg cccttggcgt gttctcgtac    60
gtgtccgaaa gatgggntgt cgtgatagct ggagagaggt tagtta                 106

<210> SEQ ID NO 69
<211> LENGTH: 79
<212> TYPE: DNA
<213> ORGANISM: Triticum aestivum
<220> FEATURE:
<221> NAME/KEY: misc_feature
<222> LOCATION: (1...79)
<223> OTHER INFORMATION: n represents a, c, g or t

<400> SEQUENCE: 69
cggacggccg ctgntgtatg ntttatgtac catctgangt cacngngtgg anangcacca    60
gctagctgct tttntctta                                                79

<210> SEQ ID NO 70
<211> LENGTH: 119
<212> TYPE: DNA
<213> ORGANISM: Triticum aestivum
<220> FEATURE:
<221> NAME/KEY: misc_feature
<222> LOCATION: (1...119)
<223> OTHER INFORMATION: n represents a, c, g or t

<400> SEQUENCE: 70 cggggggntcg anctggtgca ccncgctgta catctgcgac gncgactncn ncgtgagcca    60
gcnaggcncn tcangggaac tctttnctga ggtgggcgag atcaagaggt actccatta   119

<210> SEQ ID NO 71
<211> LENGTH: 313
<212> TYPE: DNA
<213> ORGANISM: Triticum aestivum
<220> FEATURE:
<221> NAME/KEY: misc_feature
<222> LOCATION: (1...313)
<223> OTHER INFORMATION: n represents a, c, g or t

<400> SEQUENCE: 71
cggatgctcg tacccgctgg gattccsctc tttttgaatt gnttccatct agagtaggan    60
attgnggaan cttccsctgn tnttgctgac gctgtatcnt atttgactan nanagtggat   120
tcnannacaa nagatgngaa agttctccag cctacaatag ctactcagtc tgtacggact   180
actganggca attcgctcta cganatggac aaagcancac nggaggtggt cagngcaatt   240
gtggaggcac agtctggtgg tcttgggctt gccatgaaca agatttctct tgggcctgac   300
ttgccaacta tta                                                      313

<210> SEQ ID NO 72
<211> LENGTH: 135
<212> TYPE: DNA
<213> ORGANISM: Triticum aestivum
<220> FEATURE:

<221> NAME/KEY: misc_feature
<222> LOCATION: (1...135)
<223> OTHER INFORMATION: n represents a, c, g or t

<400> SEQUENCE: 72 cggggannntg ccgctgctcg aagtacccga agtgcgccgg tggaacgcct gagtttgttt    60
cgcgccgaat ctggcaagtt tgantgggca ataacggaat aatgagctga ggaacnangc   120
atattgtttc tttta                                                    135

<210> SEQ ID NO 73
<211> LENGTH: 399
<212> TYPE: DNA
<213> ORGANISM: Triticum aestivum
<220> FEATURE:
<221> NAME/KEY: misc_feature
<222> LOCATION: (1...399)
<223> OTHER INFORMATION: n represents a, c, g or t

<400> SEQUENCE: 73
cggaccacag ctcgctgacg gacgtcgtgt acgtctccct ggctcaggca aacgagatat    60
acggttcttc ctcgtcgtca gcgtttgtgg cctagctaga tactgtcgca natcatcctt   120
gagagattat atacatgatc tgggatccat ttcacggaaa ccttgagcac caccctgatn   180
ggagggacct tccccgctg tcgctgctgc atcctgnatg gcaaggcagg acatgaggtc    240
tgaagaattc aacaagttct gaagctgtgt aaattgcaat ttgtagatat agcatcatca   300
tatatanggg cctcnttgna ggaatgtaaa tagnaaatat gtatacntag aacngtaaga   360
cttgcancan gtgcaanatt gcacggggtg attcattta                          399

<210> SEQ ID NO 74
<211> LENGTH: 132
<212> TYPE: DNA
<213> ORGANISM: Triticum aestivum
<220> FEATURE:
<221> NAME/KEY: misc_feature
<222> LOCATION: (1...132)
<223> OTHER INFORMATION: n represents a, c, g or t

<400> SEQUENCE: 74
cggggacgtg ccgctgctcg agtacccgag tgcgccgtgg acgcctgtag tttgtttcgc    60
gccagatctg gcaagtttga gtgggcnata acagaataat gagctgagga acaatancat   120
aatgtttctt ta                                                       132

<210> SEQ ID NO 75
<211> LENGTH: 283
<212> TYPE: DNA
<213> ORGANISM: Triticum aestivum

<400> SEQUENCE: 75
cggcgagtgc atgttgtagt gtggttcaga aggtcaatgc accgtgcatg tgctccaagg    60
tcaccaagga gattgagaag gtggtatgca tggataaggt ggtgtatgtc gctgattact   120
gcaagaatcc actcaaacct ggctccgact gtggcagtta ccatgtccca tctcaaggcc   180
aatagatgga tgttttgtat ctggtaatca aaggagaaat gttgatttag ttcctaggcc   240
tctatgttga ctggattccg cttttatgat atgtgatagg tta                     283

<210> SEQ ID NO 76
<211> LENGTH: 125
<212> TYPE: DNA
<213> ORGANISM: Triticum aestivum

```
<220> FEATURE:
<221> NAME/KEY: misc_feature
<222> LOCATION: (1...125)
<223> OTHER INFORMATION: n represents a, c, g or t

<400> SEQUENCE: 76
cggttctatc atatgctacc tactactcga tcgatcgatt ggtccagaag actatgctcg       60
aganatgaga caaccatcga tcgatatacn tatgtgtgtc cagattgtgc tttgtgcttg      120
tctta                                                                  125

<210> SEQ ID NO 77
<211> LENGTH: 313
<212> TYPE: DNA
<213> ORGANISM: Triticum aestivum
<220> FEATURE:
<221> NAME/KEY: misc_feature
<222> LOCATION: (1...313)
<223> OTHER INFORMATION: n represents a, c, g or t

<400> SEQUENCE: 77
cggctatttt tctggctcat aggttcgtgt ggagaatgcc gagatgcctc tagcgcatat       60
tgcaattgct ttcaagggtt catcctggac tgaccctagc tctattcctc ttatggtgac      120
ccaaagcata ttgggatctt ggaatangag catcggcgta gggaactgct caggntctgc      180
tttagctcgt ggcatcagcn atggtganct agctgagaac ttgatggcat tcaacactaa      240
ctatcgcgat acaggattat ttggcatcta tactantgct ccgcctgacn cactacatga      300
cctgtcacgg tta                                                         313

<210> SEQ ID NO 78
<211> LENGTH: 413
<212> TYPE: DNA
<213> ORGANISM: Triticum aestivum
<220> FEATURE:
<221> NAME/KEY: misc_feature
<222> LOCATION: (1...413)
<223> OTHER INFORMATION: n represents a, c, g or t

<400> SEQUENCE: 78
cgggggcanc gnggaggggg tcctnntgga cacgccgcct agntcggaca angagtgcga       60
ncaggtccag cttccgcgcc tcgatccncg gttcacaccg ncanggtgtt cnctnccttg      120
atgagcctcn acgagtgnaa acgggcgcca cggcgagcat tgctgcaaac tacgnggacn      180
aggtggggna cggngctgga tgtgcggata cggtattgca nccgaggaca gctcaccacg      240
ccctagctct atgtattctt ctcgccacta catcaccacg ncctacangg cgtagagtag      300
gatgntgatg ttggtagcga agagataata nnggggatgg canangtgaa taatcccctc      360
catgctcgga gggacacgga aacttttgt tccnanacca gcngtacttg tta             413

<210> SEQ ID NO 79
<211> LENGTH: 80
<212> TYPE: DNA
<213> ORGANISM: Triticum aestivum
<220> FEATURE:
<221> NAME/KEY: misc_feature
<222> LOCATION: (1...80)
<223> OTHER INFORMATION: n represents a, c, g or t

<400> SEQUENCE: 79
cgggaaggga tagtagatga tgaaatatgt gtnncttttc ntggnaagtt catgttccaa       60
taatccggga ggtttattta                                                   80
```

```
<210> SEQ ID NO 80
<211> LENGTH: 172
<212> TYPE: DNA
<213> ORGANISM: Triticum aestivum

<400> SEQUENCE: 80
tacatgggca cactcacgcc accgattgaa gggtatattg aaaaggtgcg agatgctgcc      60
aagcaagtat tcagtgtaag gagaaacttc gctgagtccg attcaacatg ggaggaaaga     120
gtcttctcca tacaagatgc tgagagttta gacgccttct tatgctcctt ta             172

<210> SEQ ID NO 81
<211> LENGTH: 124
<212> TYPE: DNA
<213> ORGANISM: Triticum aestivum

<400> SEQUENCE: 81
cggttcatat catatgctac ctactactcg atcgatcgat tggtccagag actatgctcg      60
agagatgaga caaccatcga tcgatataca tatgtgtgtc cagattgtgc tttgtgcttg     120
tctt                                                                  124

<210> SEQ ID NO 82
<211> LENGTH: 260
<212> TYPE: DNA
<213> ORGANISM: Triticum aestivum
<220> FEATURE:
<221> NAME/KEY: misc_feature
<222> LOCATION: (1...260)
<223> OTHER INFORMATION: n represents a, c, g or t

<400> SEQUENCE: 82
ccggntctga ccggacgagg aanatgatgg tgcttggcgc ggcgcaccag gtggacacat      60
ggttcacatt tgacctccca gggtaatcgt ctctactttg cccaggcagc attgtagtgc     120
tgacactcgt gcnactgtct agatcctaga gagtactatn tgtatctgcg ccgaatgcat     180
tcatcattag ntggtgcata aaccgtctgg gaacnatttg agaataatga gttacattcc     240
taattatnat gctgaattta                                                 260

<210> SEQ ID NO 83
<211> LENGTH: 225
<212> TYPE: DNA
<213> ORGANISM: Triticum aestivum
<220> FEATURE:
<221> NAME/KEY: misc_feature
<222> LOCATION: (1...225)
<223> OTHER INFORMATION: n represents a, c, g or t

<400> SEQUENCE: 83
cggcganncc tgcnggagtg gtggganccgt tttggcgtcc atgaggcacn ttcntgccag      60
cgngancgnc tgctgctttg ngncggggac ggctaattnn nggggccagn ngcatcgccg     120 ngnnggncttctt cttnatcncc tcgtgggtan atanatgatt tgtgtantcg caactctgat     180
atncnacctg ctttntgtcg ctaagcaagg aanatnccgt catta                     225

<210> SEQ ID NO 84
<211> LENGTH: 160
<212> TYPE: DNA
<213> ORGANISM: Triticum aestivum
<220> FEATURE:
<221> NAME/KEY: misc_feature
<222> LOCATION: (1...160)
<223> OTHER INFORMATION: n represents a, c, g or t
```

<400> SEQUENCE: 84
cggcgntgcg angangagct tcaccganct gccagaggag gcggcgctgt tcaggananc    60
actganctgc ngatgctagt ccggatgggn tctagcttcc tagncccant ggatgnncca   120
tacgacntgt ngtgntgana tcagttttgc acttntntgg                          160

<210> SEQ ID NO 85
<211> LENGTH: 202
<212> TYPE: DNA
<213> ORGANISM: Triticum aestivum
<220> FEATURE:
<221> NAME/KEY: misc_feature
<222> LOCATION: (1...202)
<223> OTHER INFORMATION: n represents a, c, g or t

<400> SEQUENCE: 85
cggtgnggag acctangcac gcctagctag tgtaagagga tctcttcttc ggtctgcatc    60
tgtctatctt attcagagca gataacgaag actagtctat tttaccgtct aagtgcatgt   120
gatgatctgt agtaacaatg gattgtgatc gttaggcgtg gctcatggat tcgatcgata   180
ttcttccttg ttgacatgct ta                                             202

<210> SEQ ID NO 86
<211> LENGTH: 141
<212> TYPE: DNA
<213> ORGANISM: Triticum aestivum
<220> FEATURE:
<221> NAME/KEY: misc_feature
<222> LOCATION: (1...141)
<223> OTHER INFORMATION: n represents a, c, g or t

<400> SEQUENCE: 86
cggctnctgc nnancgagct tgacgatgtg cnnnaggagg tggcgntctt ganggaaanc    60
ggtgagctgc aaatgctact acacntgtgc gctaacttct tntnatcact agtatgatga   120
acatatgttg ttttgacatt a                                              141

<210> SEQ ID NO 87
<211> LENGTH: 181
<212> TYPE: DNA
<213> ORGANISM: Triticum aestivum

<400> SEQUENCE: 87
cggatgcagc agcgtgcatg cgtaagtata gacgtactac cgttgctagt tgcacgcacg    60
tagtaactac tcgtatgcat ggtcaataag aaggtactgc atgtgtatgt atacgtacac   120
attgcacagt tatcttgatc caataccagg actccgttct ggtcaatggt gttcatgttt   180
a                                                                    181

<210> SEQ ID NO 88
<211> LENGTH: 122
<212> TYPE: DNA
<213> ORGANISM: Triticum aestivum
<220> FEATURE:
<221> NAME/KEY: misc_feature
<222> LOCATION: (1...122)
<223> OTHER INFORMATION: n represents a, c, g or t

<400> SEQUENCE: 88
cgggtgctcn tagcttgctc aagggctgnt ctagggntgt ggatntctct cacttcnanc    60
ggcncntnct gggnagcatc nannacttgg annatactag ctncgacata tccttggcgt   120
ta                                                                          122

<210> SEQ ID NO 89
<211> LENGTH: 332
<212> TYPE: DNA
<213> ORGANISM: Triticum aestivum
<220> FEATURE:
<221> NAME/KEY: misc_feature
<222> LOCATION: (1...332)
<223> OTHER INFORMATION: n represents a, c, g or t

<400> SEQUENCE: 89
cggggacgac gacggcggcc tcctggtccg actcgagcca gcagccgtac cacccgccgc      60
acacccaata gcgcagccgc aaagccnagg ccaagattct gcgccgtctc tggaagaaag     120
aataagttgt gtacggaagg cgacggagac gggcgcagca gcaaccagca agcagaggaa     180
ggttgagaat gatggcgtca ctcaccgagg ggcatgtgtt gattgacagc tatgggcgtg     240
ctcattttgt tcgttcgttg attattagtt tgggaggtgg tgcgggtcgc cccgttttta     300
gtactttctg ctttggttat tactgcaaat ta                                   332

<210> SEQ ID NO 90
<211> LENGTH: 363
<212> TYPE: DNA
<213> ORGANISM: Triticum aestivum
<220> FEATURE:
<221> NAME/KEY: misc_feature
<222> LOCATION: (1...363)
<223> OTHER INFORMATION: n represents a, c, g or t

<400> SEQUENCE: 90
cggggacgac ggcggcggcc tcctggtccg actcgagcca gcagccgtac cacccgccgc      60
acacccaata gcgcagcaat cgcaaaacca agccaaggc caagcattct gcgccgtctc     120
tggaagaaag aataagttgt gtacggatgg cgacggagac gggcgcagca gcagcaagca     180
naagatcgag aaaaaaacaa gcagaagaag atcgagaatg atggcgtcac tcgctgaggg     240
gcatgtgttg attgacagct atggacggtg ctcattttgt tcgttcgttg attattagtt     300
tgggtggtgg ggcggggtcg accgttgtt agtactttct gttttggtta ttactgcaaa     360
tta                                                                  363

<210> SEQ ID NO 91
<211> LENGTH: 119
<212> TYPE: DNA
<213> ORGANISM: Triticum aestivum
<220> FEATURE:
<221> NAME/KEY: misc_feature
<222> LOCATION: (1...119)
<223> OTHER INFORMATION: n represents a, c, g or t

<400> SEQUENCE: 91
cgggcttccc ccgtggattg cattagtatc cactatgttt gtggtctatt ctttttgtct      60
caggtttttt tattccttgt tgcngtgtta tttangggag attagacgtg acatcctta     119

<210> SEQ ID NO 92
<211> LENGTH: 173
<212> TYPE: DNA
<213> ORGANISM: Triticum aestivum
<220> FEATURE:
<221> NAME/KEY: misc_feature
<222> LOCATION: (1...173)
<223> OTHER INFORMATION: n represents a, c, g or t

<400> SEQUENCE: 92

```
cggattaacg tgtttgatgt gcttttacgt ggtttgcttt attgttgcca aatcgganat      60
gcggttggnc aagtccaggt agaggtantg acgatgacat ttgatcgtct gcggagggct     120
tgcttgctct gaaccctgca tatntccctt gtgatttgng atactcgtcg tta            173
```

<210> SEQ ID NO 93
<211> LENGTH: 234
<212> TYPE: DNA
<213> ORGANISM: Triticum aestivum
<220> FEATURE:
<221> NAME/KEY: misc_feature
<222> LOCATION: (1...234)
<223> OTHER INFORMATION: n represents a, c, g or t

<400> SEQUENCE: 93

```
cggcattttc tagncgccgc ctcccngntc gctgcctatn ccccgttctc gctccaccag      60
aagcgcagct gngtcnctng tgttggcacc tgctnatacg ccanagagnn gngganctgc     120
ttgtgcatgc tcaagtcagc ncctncgaca cccactgctg ggtcaggcat ttgtctncttt    180 tggggacaat gntncngcct ttgcctctna gaatatnagg agnatccttg caca            234
```

<210> SEQ ID NO 94
<211> LENGTH: 170
<212> TYPE: DNA
<213> ORGANISM: Triticum aestivum
<220> FEATURE:
<221> NAME/KEY: misc_feature
<222> LOCATION: (1...170)
<223> OTHER INFORMATION: n represents a, c, g or t

<400> SEQUENCE: 94

```
cggcggtact agcacgcccg ttgatcacgc gntcaacgcc gncgagtgtc ctcacctacc      60
ctgctgcaga ctgcactagc agtgtgtaag aataaaataa anntggatga cctatatgtg     120
tggtggacac acgattatga atangacaac gtggtgatgt tcantcctta                170
```

<210> SEQ ID NO 95
<211> LENGTH: 293
<212> TYPE: DNA
<213> ORGANISM: Triticum aestivum
<220> FEATURE:
<221> NAME/KEY: misc_feature
<222> LOCATION: (1...293)
<223> OTHER INFORMATION: n represents a, c, g or t

<400> SEQUENCE: 95

```
cggatngcgc cggtgttctg agcttgatng canttctgat gntttcaagt cnctttnttg      60
tcgngtgagg cnnctcggta ggtacatacg cctgntnncn aacattgnnc gtcgaggngn     120
nccntgaacc ctacactcct tgtatngatc cttcattttg ggatgacatc tgcaagnnag     180
atgnntacgg aggtgggacc tgccntggtg gtgcntgctn ctgcatctta tatttgtngc    240
nanngactnn ctacgaatag tgtttggnaa taaagattca cttgggagca tta            293
```

<210> SEQ ID NO 96
<211> LENGTH: 280
<212> TYPE: DNA
<213> ORGANISM: Triticum aestivum
<220> FEATURE:
<221> NAME/KEY: misc_feature
<222> LOCATION: (1...280)
<223> OTHER INFORMATION: n represents a, c, g or t

<400> SEQUENCE: 96

```
cggatcacac nngtgttctg tgcttgattg cactttgat nctttcaacc actttgttgt      60
cntgtgaanc ntcngggagg accatacgcc tgntaaacg acgtttgcgg tgggaagtac    120
cgtgaaccct acggtcgttg tatcgatgct aagtcgtgtg atgtcttctg caagcaagat   180
aaanngggag gcggggcctg ccgnaatggt gcatgttgtt gcttcttgta caacaagaaa   240
atgaccatga atatagtgtg gaaataaaga ttgagcatta                          280
```

<210> SEQ ID NO 97
<211> LENGTH: 147
<212> TYPE: DNA
<213> ORGANISM: Triticum aestivum
<220> FEATURE:
<221> NAME/KEY: misc_feature
<222> LOCATION: (1...147)
<223> OTHER INFORMATION: n represents a, c, g or t

<400> SEQUENCE: 97

```
cggttggnaa gatgatttgg acccgattgc atttcttgtt tcctgttcgg ggtcctccat     60
gcaaaaacag gggactggtc tgtaattttc tttcctttgt gtgtcctgtt gtaactacgg   120
tgtgctagtg ctaccgatct atggtta                                       147
```

<210> SEQ ID NO 98
<211> LENGTH: 423
<212> TYPE: DNA
<213> ORGANISM: Triticum aestivum
<220> FEATURE:
<221> NAME/KEY: misc_feature
<222> LOCATION: (1...423)
<223> OTHER INFORMATION: n represents a, c, g or t

<400> SEQUENCE: 98

```
cggcacgaca gcatagtgat gaggcaagga ccttcgtgac ctggtcctcg ttggtgtaga     60
cnttctcagg gacatatcat tgctgcaagt ggcaaggtca agaaaatgtt gcacaatgcc   120
aagaatggca catcaatagc acacctcctt cgtttgtgcg agctgcacta tgacgccgca   180
ntgaccatcc tcaacatctc cnacaccatg ctcaaggaca accacgggcc cnaaggtggt   240
gaaaaatatg gaccccgtc ctattattta cccgactgtg tgggtatggc atccagcctt    300
gtcnactact gtgggcatga gcttgttgat atgcctgggc aggaggcgtt gtacaaacaa   360
aatattgagc ttggcgatct gggtagcctc aacnttgcct tggtggcgcc atattgggat   420
tta                                                                 423
```

<210> SEQ ID NO 99
<211> LENGTH: 420
<212> TYPE: DNA
<213> ORGANISM: Triticum aestivum

<400> SEQUENCE: 99

```
cggcttcctc atctctcccg ccgcatttgc ggccaacccg cagatgtact tccagctcct     60
ccacaacgca ggcgctgcag cggctgccgc cgcctttgca gcctagagag gcaaggcacg   120
ccagggtttg atgccaagtt agtggcagta cgctaggttg ctacctagta tggagttagg   180
gatagggact gatctttggt acttgggcat gtactgccca agctaagcta gtttcaatca   240
agttcaggag tagggactgc atctttgca  cttgggcacg tatgtattgc ccaagctaag   300
ctggtgtcaa tcaggttcaa tgtcatcttc tgtacctggg ctgtgcgtgt atgttcggcc   360
atgttactac cgtgtcaaca gtctgaagct actctctcta atgtaaagta gtaaccgtta   420
```

<210> SEQ ID NO 100
<211> LENGTH: 198
<212> TYPE: DNA
<213> ORGANISM: Triticum aestivum
<220> FEATURE:
<221> NAME/KEY: misc_feature
<222> LOCATION: (1...198)
<223> OTHER INFORMATION: n represents a, c, g or t

<400> SEQUENCE: 100
cgggcccaag acaaacctct attcctactc agtagtacag tactattctt tttccttctc      60
gacgtatact acagctcgat cgtgtgacgt ggggtgtggt tcctaacgat tcaatttaca     120
gctgtactgn tttgatttgt acacaaacat atacgataca ttcgaggcaa aagacgctat     180
atgtggcatc gatactta                                                   198

<210> SEQ ID NO 101
<211> LENGTH: 164
<212> TYPE: DNA
<213> ORGANISM: Triticum aestivum
<220> FEATURE:
<221> NAME/KEY: misc_feature
<222> LOCATION: (1...164)
<223> OTHER INFORMATION: n represents a, c, g or t

<400> SEQUENCE: 101
cggctcctgt gtgaaatgna tctggaagag cactacaact ctgagctttg caggatctgc      60
ancactgtag gataaatatc tagccgagcc taacaaggtt ttgctgtgct tgtacatgta     120
gaatgttcct gcggtcctgc taaaaatcag tcgactgaga ttta                      164

<210> SEQ ID NO 102
<211> LENGTH: 446
<212> TYPE: DNA
<213> ORGANISM: Triticum aestivum
<220> FEATURE:
<221> NAME/KEY: misc_feature
<222> LOCATION: (1...446)
<223> OTHER INFORMATION: n represents a, c, g or t

<400> SEQUENCE: 102
cgggggccgc gcagggggc gccacgcccg cgcagctgcc caggcggcac cacctggcct       60
tctccgtggc cgacttcgga cgggttcctc accgtgctca ggaccgcgg caccgagctg     120 ttcgagaagt cccagcccga cngccgcacg cgccaggtct tcttcttgga ccccgacggc    180
aatggtctan aagtcacaag ctcgagccca ggcgataagg aacctgctgg gagcaggaaa    240
caccttctac ttctgcgaca cccatgtagt gatgcccacc tcgagactga agatgatgga    300
agctgcacaa tttgagggaa acatccagt gccatgcgtt actccgaaat aaataaggac    360
cttactactt atatctatct gctccccatg cttgtaatct ggatatgcat gtctctggct     420
caagactgaa cttgtgctgt gtgtta                                          446

<210> SEQ ID NO 103
<211> LENGTH: 333
<212> TYPE: DNA
<213> ORGANISM: Triticum aestivum
<220> FEATURE:
<221> NAME/KEY: misc_feature
<222> LOCATION: (1...333)
<223> OTHER INFORMATION: n represents a, c, g or t

<400> SEQUENCE: 103
cggggaacga cgacggcggc ctcctggtcc gactcgagcc agcagccgta ccaccgcccg      60

```
cacacccaat agcgcagccg caaagccaag gccaagattc tgcgccgtct ctggaagaaa    120
gaataagttg tgtacggaag cgacggaga cgggcgcagc agcaaccagc aagcaggaga    180
aggttgagaa tgatggcgtc actcaccgag gggcatgtgt tgattgacag ctatgggcgt    240
gctcattttg ttcgttcgtt gattattagt ttgggaggtg gtgcgggtcg ccccgttttt    300
agtactttct gctttggtta ttactgcnaa tta                                333
```

<210> SEQ ID NO 104
<211> LENGTH: 362
<212> TYPE: DNA
<213> ORGANISM: Triticum aestivum
<220> FEATURE:
<221> NAME/KEY: misc_feature
<222> LOCATION: (1...362)
<223> OTHER INFORMATION: n represents a, c, g or t

<400> SEQUENCE: 104

```
cggggacgac ggcggcggcc tcctggtccg actcgagcca gcagccgtac cacccgccgc    60
acacccaata gcgcagcaat cgcaaaaccn aagccaaggc caagattctg cgccgtctct    120
ggaagaaaga ataagttgtg tacggatggc gacggagacg ggcgcagcag cagcaagcan    180
aagatcgaga aaaaaacang cngaagaaga tcgagaatga tggcgtcact cgctgagggg    240
catgtgttga ttgacagcta tggacggtgc tcatttttgtt cgttcgttga ttattagttt    300
gggtggtggg gcggggtcga cccgttgtta gtactttctg ttttggttat tactgcaaat    360
ta                                                                   362
```

<210> SEQ ID NO 105
<211> LENGTH: 251
<212> TYPE: DNA
<213> ORGANISM: Triticum aestivum
<220> FEATURE:
<221> NAME/KEY: misc_feature
<222> LOCATION: (1...251)
<223> OTHER INFORMATION: n represents a, c, g or t

<400> SEQUENCE: 105

```
cggaangacc nccgtgnccg actaggccaa gtannctggt ggatnagaag accgctgaga    60
tcaagatgtg cgtggaggac aagctgatga agatcctgac agaggacgag caggtgggca    120
tggagcccga cnacaaggct cgcgtggctg ccctgcagga gtgggaggag aggctcctcg    180
ccnggnagga ngccctgaag aaggaggagg agganttgga gggggcaac cagaacntgg     240 gtccctgatt a                                                         251
```

<210> SEQ ID NO 106
<211> LENGTH: 245
<212> TYPE: DNA
<213> ORGANISM: Triticum aestivum

<400> SEQUENCE: 106

```
cgggaagggt gctcgcgctg ccacatggc ccttctgggg cgccacctct tcgccttcct     60
cctgcccttc tacctgccca gggcgctcca gaggtactac tgcgacgacg cgtcgaccg    120 caccaacggc gatggccacg cccacgaaga taagaaggat tcctagatga tgcgccgtcc    180
gagtgttctt gtgatggctg tgcgtagccg cgttgcatct tttactccag tagattgttg    240
cttta                                                                245
```

<210> SEQ ID NO 107
<211> LENGTH: 74

```
<212> TYPE: DNA
<213> ORGANISM: Triticum aestivum
<220> FEATURE:
<221> NAME/KEY: misc_feature
<222> LOCATION: (1...74)
<223> OTHER INFORMATION: n represents a, c, g or t

<400> SEQUENCE: 107
cggtactggg ccatgcatgc atgagctata tgtgtgacan ttttatgctn cttgtgtttc    60
ncctggctcc atta                                                     74

<210> SEQ ID NO 108
<211> LENGTH: 438
<212> TYPE: DNA
<213> ORGANISM: Triticum aestivum
<220> FEATURE:
<221> NAME/KEY: misc_feature
<222> LOCATION: (1...438)
<223> OTHER INFORMATION: n represents a, c, g or t

<400> SEQUENCE: 108
cggctcctgc tgcaagatgt ccactgtcca gacccgtgcg tatcattatt ctccctgtct    60
gtgccgcgca acagcagttt cctgnagccc tgcctccatc agcttctccc tcttccttgc   120
aatcggtgag ttcagcatac aagcttcaga ttgataagct cctatgtact gctgttctag   180
acaaacaatg acaacgacgc cttcttgttt ttagnactaa ccaacatttc agagaacaaa   240
gttattgctg taagtagctt tttgaaagtt cctttcagn ctttcagtct tgggtacatg    300
aaaaaangat gtcncantct gaaanaattt ggccntgtat gtcaattcta gctgagaatt   360
actnatgatg atagcataat gagaggcntg cgtgcatgag tttacggant tacgccatga   420
cttntttccc ttcctta                                                 438

<210> SEQ ID NO 109
<211> LENGTH: 201
<212> TYPE: DNA
<213> ORGANISM: Triticum aestivum
<220> FEATURE:
<221> NAME/KEY: misc_feature
<222> LOCATION: (1...201)
<223> OTHER INFORMATION: n represents a, c, g or t

<400> SEQUENCE: 109
cgggaatcct ccccaggntc ggcggcggcg ggcctggtta cgcggcatgc ccctgccnca    60
gcgcggcgtc ggcggcgcgc ctgggatcct gcatcacccg agatggcnac natgctttct   120
catggaactc caggcgcatg ttcagttcaa atgagaaaca tctgcctgca atatctgacc   180
cnaaaattga gactgcattt a                                            201

<210> SEQ ID NO 110
<211> LENGTH: 203
<212> TYPE: DNA
<213> ORGANISM: Triticum aestivum
<220> FEATURE:
<221> NAME/KEY: misc_feature
<222> LOCATION: (1...203)
<223> OTHER INFORMATION: n represents a, c, g or t

<400> SEQUENCE: 110 cgggggganga agaanacatt cagcntgtca ctgcagtgna caaggtcgtt catgnaacca    60
caacatgtgn gagggtnagc ttgngctgnn tgtccacgcn acnngttgng aggtngcccc   120
atcatcgctg ttcctnatct tcccgaanct ccnccgtctc aagagagttt ttaggtgtgt   180
```
gttatggaaa tggctggaag tta                                            203

<210> SEQ ID NO 111
<211> LENGTH: 141
<212> TYPE: DNA
<213> ORGANISM: Triticum aestivum
<220> FEATURE:
<221> NAME/KEY: misc_feature
<222> LOCATION: (1...141)
<223> OTHER INFORMATION: n represents a, c, g or t

<400> SEQUENCE: 111
cggctactgc gaaancgagc ttgacgatnt gccaaggagg tggcgttctt gaaggaaaac    60
ggtgagctgc aaatgctact acacatgtgc gctaacttct tanaatcact agtatgatga   120
acatatgttg ttttgacatt a                                             141

<210> SEQ ID NO 112
<211> LENGTH: 375
<212> TYPE: DNA
<213> ORGANISM: Triticum aestivum
<220> FEATURE:
<221> NAME/KEY: misc_feature
<222> LOCATION: (1...375)
<223> OTHER INFORMATION: n represents a, c, g or t

<400> SEQUENCE: 112
cgggctnagg aacccgcggc acccagcttg ttcgagaaag tcccagcccg nacngccgcn    60
cgcgccaggt ncttcttctt cgaccccgac ggcnatggtc tagaantcac nggctcgagt   120
ccaggcgacn ngnaangtgc cgcgagcacg aaacaccttc tacttctgcg acncccatgt   180
anngattacc cacctcgagg ctgaagatga tggaanctgc atatctgaga gaaaacatcc   240
agtgccatgc tctactccca aanaaataat gaccttgcta cctatatcta tctatatgct   300
ccccatgcct gtnatctgga tatgcatgtc tgagactgaa tctganctcg tgctgtgtgt   360
nacaacatca agtta                                                    375

<210> SEQ ID NO 113
<211> LENGTH: 257
<212> TYPE: DNA
<213> ORGANISM: Triticum aestivum
<220> FEATURE:
<221> NAME/KEY: misc_feature
<222> LOCATION: (1...257)
<223> OTHER INFORMATION: n represents a, c, g or t

<400> SEQUENCE: 113
cgggcccagg cggctcncca ccaccaccct tctgatagca gcccagcata tccaccacan    60
cnaataatgc aggcctaaat gttggctcan gagcttactt gtgtgancat cctggctgtt   120
gagagtaccc cttgctacag tngtacncac actactgaaa ataattgtcc tgtatctctt   180
ggagatgact gtatgcagtc ttacctagtt acntggcact tatatngntt gnactgacta   240
aatgcaatta tcggtta                                                  257

<210> SEQ ID NO 114
<211> LENGTH: 102
<212> TYPE: DNA
<213> ORGANISM: Triticum aestivum
<220> FEATURE:
<221> NAME/KEY: misc_feature
<222> LOCATION: (1...102)
<223> OTHER INFORMATION: n represents a, c, g or t

<400> SEQUENCE: 114

```
cggaaagaag cgctgtgttc tccntctcag tgtatatttg cgtcgcgct gggttcctct    60 tgctgccagt ttagtcttag gttttgtgag aaatgcagtt ta                     102

<210> SEQ ID NO 115
<211> LENGTH: 164
<212> TYPE: DNA
<213> ORGANISM: Triticum aestivum
<220> FEATURE:
<221> NAME/KEY: misc_feature
<222> LOCATION: (1...164)
<223> OTHER INFORMATION: n represents a, c, g or t

<400> SEQUENCE: 115
cggcagcaca tgcagctgct ngaccagtgg ggtacaatcc agatgtgctg ccctaggaac    60
atttactgtt gcgggttcgg tggcgcattg gccagtgcac ctgcgccatc cattgagcct   120
tgatgtgtgg ttctattctc ctcgaggtag aangctcgac atta                   164

<210> SEQ ID NO 116
<211> LENGTH: 263
<212> TYPE: DNA
<213> ORGANISM: Triticum aestivum
<220> FEATURE:
<221> NAME/KEY: misc_feature
<222> LOCATION: (1...263)
<223> OTHER INFORMATION: n represents a, c, g or t

<400> SEQUENCE: 116
cgggctcgcg tcccgtctac gactacagga ccacatcacc ntcgtcgtcg gccaggtagc    60
aanctcttcg ncgccgagct cgaggccatc tggcgncagc gccgcccagg gactagcgcc   120
tctgcctctc tgcctctctc tcgacctcgt tcgccaacca ccacatgcat gtacaaccct   180
agtactgcta ctactacttc ngctacagtg atcatcagcc agcaacagtg cacagtgagg   240
aggaggaaga gaggaggaga tta                                          263

<210> SEQ ID NO 117
<211> LENGTH: 148
<212> TYPE: DNA
<213> ORGANISM: Triticum aestivum
<220> FEATURE:
<221> NAME/KEY: misc_feature
<222> LOCATION: (1...148)
<223> OTHER INFORMATION: n represents a, c, g or t

<400> SEQUENCE: 117
cggttggcag atgatttgga cccgattgca tttcttgttt cctgttcggg gtcctccatg    60
cnaaaaacag gggactggtc tgtaattttc tttcctttgt gtgtcctgtt gtaaactacg   120
gtgtgctagt gctaccgatc tatggtta                                     148

<210> SEQ ID NO 118
<211> LENGTH: 117
<212> TYPE: DNA
<213> ORGANISM: Triticum aestivum
<220> FEATURE:
<221> NAME/KEY: misc_feature
<222> LOCATION: (1...117)
<223> OTHER INFORMATION: n represents a, c, g or t

<400> SEQUENCE: 118
cggtattgcc cggatntgct gctggantgt cgaaaagact attttgagca ncccgtaagg    60
tgacatctgc tggttttcng tgcncntttt tcactaatcn tatncgtagn ngagtta     117
```

```
<210> SEQ ID NO 119
<211> LENGTH: 324
<212> TYPE: DNA
<213> ORGANISM: Triticum aestivum
<220> FEATURE:
<221> NAME/KEY: misc_feature
<222> LOCATION: (1...324)
<223> OTHER INFORMATION: n represents a, c, g or t

<400> SEQUENCE: 119
cggacatcac actaaaagct tccnacatgc atcctgggca nccactccgc tgaagctgcc      60
gttaggcttg cagtaccttt ttgtttctga cccaactatt tgcatgaaca atagggatgg     120
ctatattgtt tacctgactg cgagggagaa gtatatgcat tctaagtcat ggattattgc     180
tattgatttg aaaaagcgcn aggtgcaaag tgtgnttctg tctggtcctg tacctccgcc     240
aatgccgcgc attgacacta actactgcac ttgtagtatc tcccagtact gtaccagcac     300
ttcaacagta tcaggtggta ctta                                            324

<210> SEQ ID NO 120
<211> LENGTH: 435
<212> TYPE: DNA
<213> ORGANISM: Triticum aestivum
<220> FEATURE:
<221> NAME/KEY: misc_feature
<222> LOCATION: (1...435)
<223> OTHER INFORMATION: n represents a, c, g or t

<400> SEQUENCE: 120
cgggaacaga tcaatgtccc tgctnagctg acagcaaaaa gtatccnccc tacatggaat      60
cgaaaggaan gctaccnttc gncttccntn ctaggaaaaa tttatgncta agcaccaant     120
ttgcaatctg agaaagttga accagtctca gatntcgttg gacccgcgtt tcacggcttn     180
gngcagcatc ttngggatnc angtacctga acctctggac nggccgttat cgngngtact     240
tgaacnagng tgggcctctg attgnccctc aanacnagga cgaaanagac ctgatgttcn     300
nagaactcta cctaaaanac aantacnngc tctncgangc cgctgaattc gagcaaacnc     360
agaggaatct tgacgaattg ttcnacgagg catgcacaat ctaccagatc gtctangaga     420
nagctnngag gttta                                                      435

<210> SEQ ID NO 121
<211> LENGTH: 164
<212> TYPE: DNA
<213> ORGANISM: Triticum aestivum
<220> FEATURE:
<221> NAME/KEY: misc_feature
<222> LOCATION: (1...164)
<223> OTHER INFORMATION: n represents a, c, g or t

<400> SEQUENCE: 121
cgggcggnta ttagcggtgc ggcgggcaag ctggtcggcc acaggcgcag gcgctaccac      60
ctgcggggca tggctataaa tgttgtgttg ttttgcttga agaaaaatcc cgatgtntcc     120
aataagacaa taatacatac gtcggtccca aattacttgt ctta                      164

<210> SEQ ID NO 122
<211> LENGTH: 18
<212> TYPE: DNA
<213> ORGANISM: Artificial Sequence
<220> FEATURE:
<223> OTHER INFORMATION: Synthetic construct

<400> SEQUENCE: 122
```
tttttttttt tttttttt                                                        18

<210> SEQ ID NO 123
<211> LENGTH: 28
<212> TYPE: DNA
<213> ORGANISM: Artificial Sequence
<220> FEATURE:
<223> OTHER INFORMATION: Synthetic construct

<400> SEQUENCE: 123
aatggctaca cgaactcggt tcatgaca                                             28

<210> SEQ ID NO 124
<211> LENGTH: 28
<212> TYPE: DNA
<213> ORGANISM: Artificial Sequence
<220> FEATURE:
<223> OTHER INFORMATION: Synthetic construct

<400> SEQUENCE: 124
aagtatcgtc acgaggcgtc ctactgcg                                             28

<210> SEQ ID NO 125
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1...20)
<223> OTHER INFORMATION: n represents a, c, g or t

<400> SEQUENCE: 125
actcggttca tgacacggnn                                                      20

<210> SEQ ID NO 126
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1...20)
<223> OTHER INFORMATION: n represents a, c, g or t

<400> SEQUENCE: 126
aggcgtccta ctgcgtaann                                                      20

<210> SEQ ID NO 127
<211> LENGTH: 52
<212> TYPE: DNA
<213> ORGANISM: Artificial Sequence
<220> FEATURE:
<223> OTHER INFORMATION: Synthetic construct

<400> SEQUENCE: 127
taggtaatac gactcactat agggcgaatt gggtactcgg ttcatgacac gg                  52

<210> SEQ ID NO 128
<211> LENGTH: 18
<212> TYPE: DNA
<213> ORGANISM: Artificial Sequence
<220> FEATURE:
<223> OTHER INFORMATION: Synthetic construct

```
<400> SEQUENCE: 128
aggcgtccta ctgcgtaa                                                  18

<210> SEQ ID NO 129
<211> LENGTH: 20
<212> TYPE: DNA
<213> ORGANISM: Artificial Sequence
<220> FEATURE:
<223> OTHER INFORMATION: Synthetic construct

<400> SEQUENCE: 129
taatacgact cactataggg                                                20

<210> SEQ ID NO 130
<211> LENGTH: 16
<212> TYPE: DNA
<213> ORGANISM: Artificial Sequence
<220> FEATURE:
<223> OTHER INFORMATION: Synthetic construct

<400> SEQUENCE: 130
ggccgagggc gatctc                                                    16

<210> SEQ ID NO 131
<211> LENGTH: 19
<212> TYPE: DNA
<213> ORGANISM: Artificial Sequence
<220> FEATURE:
<223> OTHER INFORMATION: Synthetic construct

<400> SEQUENCE: 131
ggccactctt ctcccagac                                                 19

<210> SEQ ID NO 132
<211> LENGTH: 16
<212> TYPE: DNA
<213> ORGANISM: Artificial Sequence
<220> FEATURE:
<223> OTHER INFORMATION: Synthetic construct

<400> SEQUENCE: 132
atcccctcgg gtttca                                                    16

<210> SEQ ID NO 133
<211> LENGTH: 22
<212> TYPE: DNA
<213> ORGANISM: Artificial Sequence
<220> FEATURE:
<223> OTHER INFORMATION: Synthetic construct

<400> SEQUENCE: 133
gctcaagatg aagccgaaca tg                                             22

<210> SEQ ID NO 134
<211> LENGTH: 19
<212> TYPE: DNA
<213> ORGANISM: Artificial Sequence
<220> FEATURE:
<223> OTHER INFORMATION: Synthetic construct

<400> SEQUENCE: 134
ttcatgctgc accctcctt                                                 19

<210> SEQ ID NO 135
<211> LENGTH: 16
```

```
<212> TYPE: DNA
<213> ORGANISM: Artificial Sequence
<220> FEATURE:
<223> OTHER INFORMATION: Synthetic construct

<400> SEQUENCE: 135
tcgaccgacg ccaacc                                                    16

<210> SEQ ID NO 136
<211> LENGTH: 21
<212> TYPE: DNA
<213> ORGANISM: Artificial Sequence
<220> FEATURE:
<223> OTHER INFORMATION: Synthetic construct

<400> SEQUENCE: 136
gccgtagctt accagtaacc a                                              21

<210> SEQ ID NO 137
<211> LENGTH: 24
<212> TYPE: DNA
<213> ORGANISM: Artificial Sequence
<220> FEATURE:
<223> OTHER INFORMATION: Synthetic construct

<400> SEQUENCE: 137
gatttgtaca ccaacaccca gaag                                           24

<210> SEQ ID NO 138
<211> LENGTH: 15
<212> TYPE: DNA
<213> ORGANISM: Artificial Sequence
<220> FEATURE:
<223> OTHER INFORMATION: Synthetic construct

<400> SEQUENCE: 138
ccgcatgaca aataa                                                     15

<210> SEQ ID NO 139
<211> LENGTH: 19
<212> TYPE: DNA
<213> ORGANISM: Artificial Sequence
<220> FEATURE:
<223> OTHER INFORMATION: Synthetic construct

<400> SEQUENCE: 139
ggtccctggc agtggtact                                                 19

<210> SEQ ID NO 140
<211> LENGTH: 25
<212> TYPE: DNA
<213> ORGANISM: Artificial Sequence
<220> FEATURE:
<223> OTHER INFORMATION: Synthetic construct

<400> SEQUENCE: 140
ctaggtgtac atcattccct cgaaa                                          25

<210> SEQ ID NO 141
<211> LENGTH: 16
<212> TYPE: DNA
<213> ORGANISM: Artificial Sequence
<220> FEATURE:
<223> OTHER INFORMATION: Synthetic construct

<400> SEQUENCE: 141
```

-continued

```
catcctgcgt tattcg                                                   16

<210> SEQ ID NO 142
<211> LENGTH: 22
<212> TYPE: DNA
<213> ORGANISM: Artificial Sequence
<220> FEATURE:
<223> OTHER INFORMATION: Synthetic construct

<400> SEQUENCE: 142
gatggctccg atccctatgt ag                                            22

<210> SEQ ID NO 143
<211> LENGTH: 21
<212> TYPE: DNA
<213> ORGANISM: Artificial Sequence
<220> FEATURE:
<223> OTHER INFORMATION: Synthetic construct

<400> SEQUENCE: 143
ccgaatggaa acacgcggat a                                             21

<210> SEQ ID NO 144
<211> LENGTH: 18
<212> TYPE: DNA
<213> ORGANISM: Artificial Sequence
<220> FEATURE:
<223> OTHER INFORMATION: Synthetic construct

<400> SEQUENCE: 144
acgctatatg cagaaaat                                                 18

<210> SEQ ID NO 145
<211> LENGTH: 30
<212> TYPE: DNA
<213> ORGANISM: Artificial Sequence
<220> FEATURE:
<223> OTHER INFORMATION: Synthetic DNA

<400> SEQUENCE: 145
cgtgtcatga accgagttcg tgtagccatt                                    30

<210> SEQ ID NO 146
<211> LENGTH: 30
<212> TYPE: DNA
<213> ORGANISM: Artificial Sequence
<220> FEATURE:
<223> OTHER INFORMATION: Synthetic DNA

<400> SEQUENCE: 146
tacgcagtag gacgcctcgt gacgatactt                                    30
```

METHOD FOR ESTIMATING END USE QUALITIES OF WHEAT AT GROWTH STAGE

TECHNICAL FIELD

The invention relates to a method for early estimation of the end use qualities of wheat through detection of genetic markers in wheat at the early growth stage.

BACKGROUND ART

Wheat, and wheat produced in Japan in particular, is problematic in that it varies in quality depending on the production year. Reasons for this problem (particularly in Japan) include the production of many kinds of cultivar in a relatively small growing area and year-on-year weather conditions that affect seed quality. However, it is difficult to estimate the end use qualities of wheat seeds before full maturation. Hence, there is a risk of purchasing low-quality wheat. Therefore, development of technology for estimating the end use qualities of matured seeds (that will be obtained in the future) at an early stage has been desired.

Under such circumstances, certain genes correlative to the end use qualities of wheat have been reported. In particular, a high-molecular-weight glutenin subunit, puroindoline, and a waxy protein have been studied.

High-molecular-weight glutenin of wheat has long been studied as a protein that determines breadmaking qualities. Payne et al., have revealed the presence of genes encoding the high-molecular-weight glutenin on the long arm of chromosome 1 (Payne, P. I., Holt, L. M., Law, C. N. (1981) Theor Appl Genet 60: 229-236). These genes encode various types of subunits with different molecular weights. On chromosome 1D, a subunit pair (1Dx5+1Dy10) related to excellent breadmaking quality is present (Payne, P. I., Corfield, K. G., Holt, L. M., Blackman, J. A. (1981) J Sci Food Agric 32: 51-60). Comparison of the amino acid sequences between this subunit pair and a subunit pair (1Dx2+1Dy12) involved in poor breadmaking qualities has demonstrated that such types of the subunit pair are associated with gluten structure and physical characteristics (Flavell, R. B., Goldsbrough, A. P., Robert, L. S., Schnick, D., Thompson, R. D. (1989)). It has actually been reported that the gene transfer of 1Dx5 into wheat originally lacking 1Dx5 results in improvement of breadmaking qualities depending on the number of copies of the transferred gene (Barro, F., Rooke, B., Bekes, F., Gras, P., Tatham, A. S., Fido, R., Lazzeri, P. S., Shewry, P. R. and Barcelo, P. (1997) Nature Biotec 15: 1295-1299). Furthermore, the University of Florida has disclosed a method for transferring such high-molecular-weight glutenin subunit to improve breadmaking qualities (JP 2000-516097 A1).

Puroindoline has been identified as a "Grain Softness Protein," which is a starch-binding protein in soft flour (Greenwell, P. and Schofield, J. (1986) Cereal Chem. 63: 379-380; and Jolly, C. J., Rahman, S., Kortt, A. A. and Higgins, T. J. V. (1993) Theor Appl Genet 86: 589-597). This protein was initially named friabirin and was revealed to have 2 major components homologous to lipid-binding proteins known as puroindoline "a" and puroindoline "b." When the protein has been added to hard wheat flour containing no such protein, the amount of the protein added and bread hardness have exhibited inverse correlation. Accordingly, it has been demonstrated that puroindoline is a factor that affects bread quality (Dubreil, L., Meliande, S., Chiron, H., Compoint, J. P., Quillien, L. Branlard, G. and Marion, D. (1998) Cereal Chem. 75: 222-229).

Waxy proteins have also been studied as starch-binding proteins. There are 2 types of grain starch: linear amylose and amylopectin having a branched structure. A variety of grains, such as rice and barley, include "nonglutinous cultivars" containing both amylose and amylopectin molecules and "glutinous cultivars" containing no amylose. There have been no natural "glutinous" cultivars in wheat. However, the National Agricultural Research Center for the Tohoku Region has recently succeeded in developing glutinous wheat for the first time in the world. Whereas Wx proteins are present in nonglutinous wheat, Wx proteins are absent in glutinous wheat. Common wheat (Triticum aestivum L.) is a hexaploid having 3 types of Wx (Wx-A1, Wx-B1, and Wx-D1) on the chromosome arms 7AS, 4AL, and 7DS. JP Patent No. 3170595 discloses a method for confirming the presence or the absence of the expression of 3 types of Wx genes (Wx-A1, Wx-B1, and Wx-D1) in wheat through the use of a two-dimensional electrophoresis method. Furthermore, JP Patent No. 3170595 also discloses a method for producing glutinous wheat by using conventional crossing of wheat variants lacking the expression of two Wx genes. Moreover, JP 9-191819 A1 (1997) discloses bread that is produced using cereal flour including 0.5% to 30% by weight wheat flour produced from glutinous wheat. The produced bread shows no degradation in texture even when it is eaten after refrigeration or thawing following freezing. Genes encoding waxy proteins are known as waxy locus genes. JP 2003-284598 A1 discloses a method for detecting 3 types of variant waxy locus gene.

As described above, some genes governing the properties of protein and starch of wheat are known. The functions of such genes have been suggested by various kinds of test, including breadmaking tests, or examination of physical qualities of bread dough by using wheat flour milled from wheat produced by conventional breeding methods or genetic recombination.

However, the above findings merely demonstrate the relationship between specific genes and the end use qualities of wheat. Moreover, it is thought that many factors other than those above are related to the end use qualities of wheat. Therefore, it has been difficult to estimate the end use qualities of matured seeds during the growth stage before actual maturation.

DISCLOSURE OF THE INVENTION

An object of the invention is to provide a means for estimating the end use qualities of wheat flour prepared from harvested wheat at an early stage before maturation.

As a result of intensive studies to achieve the object, the inventors have discovered gene markers that exhibit changes in expression level at an early stage before maturation. Furthermore, the inventors have also discovered that such variation in expression level is associated with the end use qualities of matured seeds. Thus, the inventors have completed the invention.

Specifically, the invention includes the following inventions.

(1) A method for estimating the end use qualities of a mature wheat seed, comprising measuring the expression level of at least 1 gene selected from genes, each of which is defined by any one of the nucleotide sequences of SEQ ID NOS: 1 to 121 in immature wheat.

(2) The method according to (1), comprising measuring the expression level of at least 1 gene selected from genes, each of which is defined by any one of the nucleotide sequences of SEQ ID NOS: 1, 8, 34, 48, and 45.

(3) The method according to (1) or (2), wherein the expression level of a gene is measured by a reverse transcription quantitative PCR.

(4) A kit for estimating the end use qualities of a matured wheat seed using immature wheat, containing: at least 1 primer selected from primers of sequential 10- to 40-nucleotides, which is used for specific amplification of a gene defined by any one of the nucleotide sequences of SEQ ID NOS: 1 to 121; and/or at least 1 probe selected from probes of sequential 10- to 40-nucleotides, which specifically hybridizes to a gene defined by any one of the nucleotide sequences of SEQ ID NOS: 1 to 121.

(5) The kit according to (4), containing: at least 1 primer selected from primers of sequential 10- to 40-nucleotides, which is used for specific amplification of a gene defined by any one of the nucleotide sequences of SEQ ID NOS: 1, 8, 34, 48, and 45; and/or at least 1 probe selected from probes of sequential 10- to 40-nucleotides, which specifically hybridizes to a gene defined by any one of the nucleotide sequences of SEQ ID NOS: 1, 8, 34, 48, and 45.

(6) An array for estimating the end use qualities of a matured wheat seed using immature wheat, containing at least 1 probe of sequential 10 or more nucleotides that specifically hybridizes to at least 1 gene selected from genes, each of which is defined by any one of the nucleotide sequences of SEQ ID NOS: 1 to 121.

(7) An array for estimating the end use qualities of a matured wheat seed using immature wheat, containing at least 1 probe of sequential 10 or more nucleotides that specifically hybridizes to at least 1 gene selected from genes, each of which is defined by any one of the nucleotide sequences of SEQ ID NOS: 1, 8, 34, 48, and 45.

The invention makes it possible to estimate the end use qualities of a matured wheat seed at an early stage before maturation. Therefore, the risk of purchasing low-quality wheat can be reduced.

This description includes part or all of the contents disclosed in the specification, claims and/or drawings of Japanese Patent Application No. 2004-271391, which is a priority document of this application.

PREFERRED EMBODIMENTS OF THE INVENTION

The inventors have discovered genes that change in expression level when they are exposed to high or low temperatures during the ripening stage. The inventors have discovered that the end use qualities of a matured seed (that will be obtained in the future) can be estimated by measuring the expression levels of such genes as markers in immature wheat.

In the invention, the term "wheat" means plants belonging to the genus wheat of the family Gramineae. Examples of such wheat include common wheat, and macaroni wheat, but they are not limited thereto as long as the plants are classified as wheat. The invention is preferably used for common wheat, and particularly for *Triticum aestivum*.

A gene used as a marker in the method of the invention is a gene that is defined by any one of the nucleotide sequences of SEQ ID NOS: 1 to 121. The expression level of at least 1 gene selected from such sequences is measured. In the invention, the expression level of at least 1 and preferably 5 genes preferably selected from genes, each of which is defined by any one of the nucleotide sequences of SEQ ID NOS: 1, 8, 34, 48, and 45.

In the invention, examples of a gene defined by any one of the nucleotide sequences of SEQ ID NOS: 1 to 121 include a gene comprising any one of the nucleotide sequences of SEQ ID NOS: 1 to 121 and a gene functionally equivalent thereto. Here, the term "functionally equivalent" means that a polypeptide encoded by a subject gene possesses biological and biochemical functions equivalent to those of a polypeptide encoded by a gene comprising any one of the nucleotide sequences of SEQ ID NOS: 1 to 121.

An example of a method for preparing DNA encoding a polypeptide functionally equivalent to a polypeptide that is well known by persons skilled in the art is a method using hybridization technology (Sambrook, J et al., Molecular Cloning 2nd ed., 9.47-9.58, Cold Spring Harbor Lab. press, 1989).

Such a functionally equivalent gene generally has high homology at the amino acid sequence level. "High homology" indicates at the amino acid level, generally at least 50% or more identity, preferably 75% or more identity, further preferably 85% or more identity, and even further preferably 95% or more identity. Identity in terms of amino acid sequence or nucleotide sequence can be determined by the BLAST algorithm (Proc. Natl. Acad. Sci. U.S.A. 90: 5873-5877, 1993) of Karlin and Altschul. Specific techniques for these analysis methods are known. In addition, in this description, the term "gene" includes not only DNA but also the mRNA or cDNA thereof. The term "gene" also includes not only a full-length gene, but also EST.

Therefore, an example of a gene defined by any one of the nucleotide sequences of SEQ ID NOS: 1 to 121 encompasses a gene that contains the whole or a portion of any one of the nucleotide sequences of SEQ ID NOS: 1 to 121. The nucleotide length of such gene that contains the whole or a portion of any one of the nucleotide sequences of SEQ ID NOS: 1 to 121 is not particularly limited, as long as it encodes a functionally equivalent gene. "A portion of a nucleotide sequence" is a portion of a nucleotide sequence selected from the nucleotide sequences of SEQ ID NOS: 1 to 121 and having a nucleotide sequence length sufficient for hybridization under stringent conditions. Examples of such a portion of nucleotide sequence include an at-least-50-bases sequence, preferably an at-least-100-bases sequence, and more preferably an at-least-200-bases sequence. At-least-50-bases sequence, preferably a at-least-100-bases sequence, and more preferably an at-least-200-bases sequence which are sequential nucleotides sequence are preferred. Here, the term "sequential" means that a continuous nucleotide sequence in any one of the standard nucleotide sequences of SEQ ID NOS: 1 to 121 is contained.

In this description, the term "stringent conditions" means conditions wherein specific hybrids are formed but non-specific hybrids are not formed. Specifically, in stringent condition, only the oligonucleotide that has high homology (80% or more, preferably 90% or more, and more preferably 95% or more homology) to such gene can hybridize to a particular gene. More specifically, such conditions can be achieved by carrying out hybridization in the presence of 0.5 M to 1 M NaCl at a temperature between 42° C. and 68° C., in the presence of 50% formamide at 42° C., or in an aqueous solution at a temperature between 65° C. and 68° C. and then washing the filter using a 0.1× to 2×SSC at a temperature between room temperature and 68° C.

The expression levels of the above genes can be measured by a method generally employed in the art. A preferable method involves detecting RNA which was encoded at least 1 gene selected from genes, each of which is defined by any one of the nucleotide sequences of SEQ ID NOS: 1 to 121 from samples derived from immature wheat. Examples of "RNA detection" include not only detection of mRNA, but also detection of cDNA or cRNA converted from RNA.

An example of a method for detecting RNA encoded DNA of a gene that is defined by any one of the nucleotide sequences of SEQ ID NOS: 1 to 121 in a sample is a method using primers of sequential 10- to 40-nucleotides for specific amplification of a gene defined by any one of the nucleotide sequences of SEQ ID NOS: 1 to 121 and/or at least one probe selected from probes of sequential 10- to 40-nucleotides specifically hybridizing to a gene defined by any one of the nucleotide sequences of SEQ ID NOS: 1 to 121.

Primers for specific amplification of a gene defined by any one of the nucleotide sequences of SEQ ID NOS: 1 to 121 may be primers for amplifying a portion of any one of the nucleotide sequences of SEQ ID NOS: 1 to 121. Such primers may be primers for amplifying a nucleotide sequence between positions 27 and 176 of SEQ ID NO: 1, a nucleotide sequence between positions 150 and 250 of SEQ ID NO: 8, a nucleotide sequence between positions 12 and 80 of SEQ ID NO: 34, a nucleotide sequence between positions 40 and 149 of SEQ ID NO: 48, and a nucleotide sequence between positions 69 and 216 of SEQ ID NO: 45, for example.

Primers for specific amplification of a specific gene and a probe specifically hybridizing to a specific gene can be designed by a method generally employed in the art. Primer length is generally 10 or more nucleotides, preferably 10 to 40 nucleotides, and more preferably 15 to 30 nucleotides. Probe length is generally 10 or more nucleotides, preferably 10 to 40 nucleotides, and further preferably 15 to 30 nucleotides.

Upon the designing of such primers and a probe, it is preferable to confirm the melting temperature (Tm) thereof. The term "Tm" refers to a temperature at which 50% of an arbitrary nucleic acid chain forms a hybrid with its complementary chain. For duplex formation involving a template DNA or RNA and a primer or a probe, which leads to achievement of annealing or hybridization, annealing or hybridization temperature should be optimized. When the temperature is too low, non-specific reactions occur. The temperature is desired to be as high as possible. Therefore, the Tm of a primer or a probe to be designed is an important factor for the amplification or hybridization. For confirmation of Tm, known software for designing primers or probes can be used. An example of software usable in the invention is Amplify. Furthermore, Tm can also be confirmed by direct calculation without using software. In such a case, a calculation formula based on a Nearest Neighbor Method, a Wallance method, a GC % method, or the like can be used. In the invention, primers with an average Tm between approximately 50° C. and 70° C. and a probe with an average Tm between 55° C. and 75° C. are preferably used. Another factor that enables specific annealing or hybridization of primers or a probe is GC content. Such element is known by persons skilled in the art.

Primers are homologous to or complementary to the sequence that is used as a template when the primers are designed. Generally the sequence of a forward primer is homologous to the template sequence. The sequence of a reverse primer is complementary to the template sequence. Primers should be designed while paying attention to these facts. Designing of primers as described above is known by persons skilled in the art.

Specific examples of primers include the following primer sets:

(a) a primer set for specific amplification of a gene that is defined by the nucleotide sequence of SEQ ID NO: 1, which is composed of a forward primer consisting of the nucleotide sequence of SEQ ID NO: 130 and a reverse primer consisting of the nucleotide sequence of SEQ ID NO: 131;

(b) a primer set for specific amplification of a gene that is defined by the nucleotide sequence of SEQ ID NO: 8, which is composed of a forward primer consisting of the nucleotide sequence of SEQ ID NO: 133 and a reverse primer consisting of the nucleotide sequence of SEQ ID NO: 134;

(c) a primer set for specific amplification of a gene defined by the nucleotide sequence of SEQ ID NO: 34, which is composed of a forward primer consisting of the nucleotide sequence of SEQ ID NO: 136 and a reverse primer consisting of the nucleotide sequence of SEQ ID NO: 137;

(d) a primer set for specific amplification of a gene that is defined by the nucleotide sequence of SEQ ID NO: 48, which is composed of a forward primer consisting of the nucleotide sequence of SEQ ID NO: 139 and a reverse primer consisting of the nucleotide sequence of SEQ ID NO: 140; and (e) a primer set for specific amplification of a gene that is defined by the nucleotide sequence of SEQ ID NO: 45, which is composed of a forward primer consisting of the nucleotide sequence of SEQ ID NO: 142 and a reverse primer consisting of the nucleotide sequence of SEQ ID NO: 143.

A probe specifically hybridizing to a gene that is defined by any one of the nucleotide sequences of SEQ ID NOS: 1 to 121 may be a probe specifically hybridizing to a portion of any one of the nucleotide sequences of SEQ ID NOS: 1 to 121. Such probe may hybridize to a nucleotide sequence between positions 113 and 128 of SEQ ID NO: 1, a nucleotide sequence between positions 213 and 228 of SEQ ID NO: 8, a nucleotide sequence between positions 33 and 47 of SEQ ID NO: 34, a nucleotide sequence between positions 91 and 106 of SEQ ID NO: 48, or a nucleotide sequence between positions 178 and 194 of SEQ ID NO: 45.

Furthermore, as known by persons skilled in the art, the above primer or probe may also contain a sequence other than a portion to be annealed or hybridized, such as an additional sequence (e.g., a tag sequence). Such primer or probe to which an additional sequence is added is also included in the scope of the invention.

As a concreat example of means for measuring the expression level of a gene defined by any one of the nucleotide sequences of SEQ ID NOS: 1 to 121 in immature wheat, a method for measuring the expression level of such gene based on the level of RNA encoded by each gene in a sample derived from immature wheat is described below.

First, total RNA is extracted from a sample prepared from immature wheat. "Immature wheat" in the invention is not particularly limited, as long as the wheat is in a stage ranging from flowering after pollination to harvest. Such immature wheat is generally in the stage of 1 to 40 days after flowering and preferably in the stage of 5 to 35 days after flowering. In the invention, seeds are used as samples derived from immature wheat.

A method for extracting RNA includes a guanidine thiocyanate.caesium chloride ultracentrifugal method, a guanidine thiocyanate.hot phenol method, a guanidine hydrochloric acid method, an acid guanidine thiocyanate.phenol.chloroform method (Chomczynski, P. and Sacchi, N., (1987) Anal. Biochem., 162, 156-159), and the like.

Preferably, extracted RNA is further purified to concentrate mRNA. The purification method is not particular limited. Most mRNAs existing in the eukaryotic cell cytoplasm possess a poly(A) sequence on their 3' end. With the use of such characteristic, purification can be carried out as described below, for example. First, a biotinylated oligo(dT)

probe is added to extracted total RNA, so as to achieve adsorption of poly(A)+RNA. Next, a paramagnetic particle carrier on which streptavidin has been immobilized is added and then poly(A)+RNA is captured through the use of binding between biotin and streptavidin. Finally, after washing, poly (A)+RNA is eluted from the oligo(dT) probe. Moreover, a method that involves adsorbing poly(A)+RNA using an oligo (dT) cellulose column and then eluting and purifying the RNA may also be employed. Eluted poly(A)+RNA may be further fractionated by a sucrose density-gradient centrifugation method or the like. Poly(A)+RNA, cDNA, or cRNA obtained therefrom, and amplification products thereof, are hereinafter referred to "test nucleic acids." Examples of the method for measuring the expression level of a gene in the invention also include cases in which the levels of any of these test nucleic acids are measured.

The method for measuring the expression level of a gene is not particularly limited. The gene expression level can be measured by a method generally employed in the art. Examples of such methods include a hybridization method (e.g., Northern hybridization) and a reverse transcription PCR. In the invention, the reverse transcription PCR is preferably employed. Moreover, in the invention, the expression level of each gene is quantitatively measured preferably using a combination of quantitative PCRs such as, a real-time PCR and a competitive PCR.

In the invention, fluctuation in the expression level of a specific gene in immature wheat is measured particularly by measuring the ratio of the expression level of a specific gene to that of a gene (housekeeping gene) whose expression level does not change depending on tissues or growth stages. Examples of such gene whose expression level does not change depending on tissues or growth stages include ubiquitin gene, actin gene, tubulin gene, and ribosomal RNA gene. In the invention, the ubiquitin gene is preferably used as a standard gene.

The reverse transcription PCR involves preparing cDNA with a reverse transcriptase reaction using RNA obtained from a sample as a template and then carrying out PCR using the prepared cDNA as a template and a pair of primers.

With the competitive PCR using the same primers, a detection target contained in a test nucleic acid can be quantified by comparing the amounts of amplification products obtained with the use of a competitive template, which is an internal standard for quantification, with the amounts of amplification products obtained with the use of the test nucleic acid.

In the real-time PCR, for example, a probe that hybridizes to a specific region of a target gene is used, wherein the 5' end is labeled with a fluorescent dye (reporter) and the 3' end is labeled with a quenching dye (quencher). When this probe is used under general conditions, fluorescence of the reporter is suppressed by the quencher. Under conditions in which the fluorescence probe can completely hybridize to a target gene, PCR is carried out using TaqDNA polymerase. As an elongation reaction proceeds by Taq DNA polymerase, the fluorescence probe is hydrolyzed from the 5' end by the exonuclease activity, the reporter dye is liberated, and then fluorescence is emitted. In the real-time PCR, the initial amount of template DNA is quantified by real-time monitoring of fluorescence intensity.

For the real-time PCR, the SYBR™ Green method or TaqMan™ method can be used, for example. Reaction cycles employed for the real-time PCR consist of 50° C. for 2 minutes, 95° C. 10 minutes, and 40 cycles of 95° C. for 15 seconds and 60° C. for one minute, for example. The obtained results can be standardized using 18s ribosome RNA, for example.

To detect whether or not a specific amplification occurs after the above amplification, known means of specifically detecting an amplified product obtained by an amplification can be used. For example, detection can be achieved by causing a labeling substance such as a radioactive isotope, a fluorescent substance, or a light-emitting substance to act on dNTP that is incorporated during an amplification process and then detecting the labeling substance. As a radioactive isotope, $^{32}P$, $^{125}I$, $^{35}S$, or the like can be used. As a fluorescent substance, fluorescein (FITC), sulforhodamine (TR), tetramethylrhodamine (TRITC), or the like can be used. Furthermore, as a light-emitting substance, luciferin or the like can be used.

Types of these labeling substances, methods for introducing these labeling substances are not particularly limited. Various conventionally known means for such purposes can be used. An example of a method for introducing a labeling substance is a random-prime method using radioactive isotopes.

A method for observing an amplification product incorporating labeled dNTP may be any method, as long as it is a method known in the art for detecting the above labeled substance. For example, when a radioactive isotope is used as a labeling substance, radioactivity can be measured using a liquid scintillation counter, a γ-counter, or the like. When fluorescence is used for labeling, the fluorescence can be detected using a fluorescence microscope, a fluorescence plate reader, or the like.

With the method of the invention, a hybridization is carried out using the above probe and then the specific binding thereof is detected, so that the expression level of each gene can also be measured. A hybridization should be carried out under conditions in which a probe specifically binds only to a nucleotide sequence derived from a specific gene; that is, stringent conditions. Such stringent conditions are known in the art and are not particularly limited. When hybridization is carried out, an appropriate label such as a fluorescence label (e.g., FAM), a radioactive label, an enzyme label, a biotin label, or the like can be added to a probe.

In the invention, the expression level of a gene can also be measured by causing a labeled probe to come into contact with a test nucleic acid obtained from immature wheat so that they can hybridize to each other. The phrase "so that they can hybridize to each other" means that this step is performed under the above-described stringent conditions; that is, an environment (temperature and salt concentration) in which specific binding occurs. Specifically, samples or test nucleic acids are carried by appropriate carriers such as slide glass, membranes, microtiter plates, or the like. Labeled probes are added, thereby causing the probes to come into contact with the test nucleic acids and thus performing a hybridization. Unhybridized probes are removed and then levels of labeled probes hybridizing to the test nucleic acids are detected. The use of the concentrations of such labels as indicators enables quantitative detection. Examples of detection methods using labeled probes include a Southern hybridization method, a Northern hybridization method, and a FISH (fluorescence in situ hybridization) method.

In the invention, examples of a method for detecting at least one test nucleic acid include array methods such as a microarray and a macroarray. In such cases, detection can be performed by the following method. Specifically, probes specifically hybridizing to test nucleic acids are carried by appropriate carriers such as slide glass, membranes and microtiter plates. After labeling the test nucleic acids, a hybridization with the probes is performed. Unhybridized test substances are removed, and then the labels of the test nucleic acids hybridizing to the probes are detected. The use of the concentrations of such labels as indicators also enables quantitative detection.

Double-stranded nucleic acids (hybrids) formed by hybridization of probes with samples or test nucleic acids can also be detected without labeling probes or test nucleic acids. Double-stranded nucleic acids can be detected using a fluorescent dye or the like that specifically binds to a double-stranded portion of a nucleic acid, for example. An example of such dye is a fluorescence intercalator or the like as disclosed in JP 2002-181816 A1.

When hybridization is carried out in the measurement of the expression level of a gene, a test nucleic acid may be DNA or RNA. When detection with high sensitivity is required, it is desirable to use RNA as a test nucleic acid.

To carry out measurement with high sensitivity, it is preferable to combine an amplification and a hybridization, that is, to carry out an amplification using primers and then carry out hybridization using probes for the obtained amplification products. When such combination is used, a primer and a probe can be designed by persons skilled in the art and specific examples therefor are as described above.

An array in the invention can be prepared according to known technology such as a method disclosed in "DNA Microarrays and the Latest PCR Method" (Masaaki Muramatsu and Hiroyuki Nawa (editorial supervisor), Shujunsha, issued on March, 2003), for example. An array method using this method can be carried out in reference to this document.

According to the method of the invention, the end use qualities of a matured wheat seed are estimated by measuring the expression level of at least 1 gene defined by any one of the nucleotide sequences of SEQ ID NOS: 1 to 121 in immature wheat.

Matsuki et al., have reported that exposure of wheat to high temperatures during the ripening stage results in longer amylopectin side-chain lengths (Matsuki, J., Yasui, T., Kohyama, K., and Sasaki, T. (2003) Cereal Chem. 80(4): 476-480). Shi and Scib have reported that amylopectin in wheat grown at low temperatures often has shorter side-chain lengths, while reporting that a starch gelatinization temperature has a correlation with amylopectin side-chain length (Shi, Y. C., and Seib, P. A. (1995) Carbohydr. Polym. 26: 141-147)). Furthermore, Shibanuma et al, have reported that amylopectin side-chain length of starch affects udon qualities (Shibanuma, K., Takeda, Y., Hizukuri, S., and Shibata, S. (1994) Carbphydr. Polym. 25: 111-116). Furthermore, it has been reported that exposure of wheat to high temperatures during the ripening stage results in an increased amylase content (Tester, R. F., Debon, S. J. J., Davies, H. V., and Gidley, M. J. (1995) J. Sci. Food Agric). Moreover, Stone and Nicholas have concluded that some cultivars exhibit no changes in the ratio of glutenin to gliadin even when they are subjected to high-temperature stress, while other cultivars exhibit drastic decreases in such ratio (Stone, P. E., and Nicholas, M. E. (1994) Aust. J. Plant Physiol. 21: 887-900). In contrast, Blumenthal et al. have demonstrated that exposure of wheat to high temperatures of 35° C. or higher during the ripening stage results in poor dough qualities because of genetic modification (Blumenthal, C. S., Barlow, E. W. R., and Wrigley. C. W. (1993) J. Cereal Sci. 18: 3-21). Moreover, Blumenthal et al., have concluded that fragile dough resulting from exposure of wheat to high-temperature stress during the ripening stage is due to the decreased ratio of glutenin to gliadin and the decreased proportion of a large glutenin polymer (Blumenthal, C., Bekes, F., Gras, P. W., Barlow, W. R., and Wrigley, C. W. (1995) Cereal Chem. 72(6): 539-544). DuPont et al., have reported that under conditions wherein no additional fertilizer is provided after flowering, protein content and ω-gliadin levels are increased due to high temperatures (DuPont, F. M., Altenbach, S., Chan, R., Cronin, K., and Lieu, D. (2000) in: Shewry, P. R. and Tatham, A. S. (Eds.), Gluten Royal Society of Chemistry, Cambridge, pp. 488-491). The above findings are summarized in Table 1.

TABLE 1

Relationship between temperature stress during ripening stage and qualities of matured seeds

| | Component characteristics | End use qualities |
| --- | --- | --- |
| High temperature | Increased amylose content<br>Longer amylopectin side-chain length<br>Increased starch gelatinization temperature<br>Increased protein content<br>Decreased ratio of glutenin to gliadin<br>Decreased level of large glutenin polymer | Poorer udon qualities<br>Poorer dough qualities<br>More fragile dough |
| Low temperature | Increased level of amylopectin having short side-chain<br>Lowered starch gelatinization temperature<br>Lower-molecular-weight amylose and amylopectin | Poorer breadmaking qualities and udon qualities |

The inventors have discovered that the end use qualities of a matured seed (that will be obtained in the future) can be estimated by measuring the expression level of a gene that is defined by any one of the nucleotide sequences of SEQ ID NOS: 1 to 121 above in immature wheat according to the above method, calculating the ratio of the expression level of a gene to the expression level of a housekeeping gene such as ubiquitin gene, and then comparing the obtained result with a result obtained by exposing wheat to high temperatures or low temperatures during the ripening stage.

The method for estimating the end use qualities of a matured wheat seed based on the expression level of each gene will be described below.

First, the expression level of a gene that is defined by any one of the nucleotide sequences of SEQ ID NOS: 1 to 121 in immature wheat is measured. The ratio of expression level of the gene to that of a housekeeping gene was calculated. Subsequently, the expression level ratio is compared with the expression level ratio for the gene in wheat exposed to high temperatures or low temperatures during the ripening stage to that of a housekeeping gene. As a result, when the expression level ratio of a gene in immature wheat is analogous to the expression level ratio of the gene in wheat exposed to high temperatures during the ripening stage, the end use qualities of a matured seed that will be obtained in the future from the immature wheat are analogous to those of a matured seed that is obtained from wheat exposed to high temperatures during the ripening stage. Specifically, poorer udon qualities, poorer dough qualities, and more fragile dough can be estimated. Conversely, when the expression level ratio of a gene of immature wheat is analogous to the expression level ratio of the gene in wheat exposed to low temperatures during the ripening stage, it can be estimated that the end use qualities of a matured seed that will be obtained in the future from the immature wheat will be analogous to those of a matured seed that is obtained from such wheat exposed to low temperatures during the ripening stage; that is, poorer breadmaking qualities and poorer udon qualities.

More specifically, in immature wheat, it can be estimated that a matured seed that will be obtained in the future will possess the qualities of a matured seed that is obtained from wheat exposed to high temperatures during the ripening stage when: the expression level of a gene defined by the nucleotide sequence of SEQ ID NO: 1 is 0.06 to 0.24 times the expression level of ubiquitin gene; the expression level of a gene defined by the nucleotide sequence of SEQ ID NO: 8 is 0.8 to 3.2 times the same; the expression level of a gene defined by the nucleotide sequence of SEQ ID NO: 34 is 0.45 to 1.8 times the same; the expression level of a gene defined by the nucleotide sequence of SEQ ID NO: 48 is 0.24 (or higher) times the same; or the expression level of a gene defined by the nucleotide sequence of SEQ ID NO: 45 is 0.0015 to 0.006 times the same. Specifically, it can be estimated that the matured seed that will be obtained in the future will possess characteristics of high amylose content, long amylopectin side-chain length, high starch gelatinization temperature, high protein content, a low ratio of glutenin to gliadin, and a low high molecular weight glutenin polymer level.

Furthermore, in immature wheat, it can be determined that a matured seed that will be obtained in the future will possess the end use qualities of a matured seed that is obtained from wheat exposed to low temperatures during the ripening stage when: the expression level of a gene that is defined by the nucleotide sequence of SEQ ID NO: 1 is 0.24 (or higher) times the expression level of ubiquitin gene; the expression level of a gene that is defined by the nucleotide sequence of SEQ ID NO: 8 is 3.2 (or higher) times the same; the expression level of a gene that is defined by the nucleotide sequence of SEQ ID NO: 34 is 0.45 (or lower) times the same; the expression level of a gene that is defined by the nucleotide sequence of SEQ ID NO: 48 is 0.06 (or lower) times the same; or the expression level of a gene that is defined by the nucleotide sequence of SEQ ID NO: 45 is 0.0015 (or lower) times the same. Specifically, it can be estimated that the matured seed that will be obtained in the future will possess characteristics of low amylose content, short amylopectin side-chain length, low starch gelatinization temperature, low protein content, and low-molecular-weight amylose and amylopectin.

The end use qualities of wheat flour that is obtained from matured seeds can be estimated based on a combination of the above characteristics and conventional findings summarized in Table 1.

The invention also relates to a kit for estimating the end use qualities of a matured wheat seed with the use of immature wheat. The kit contains: at least one primer that is selected from 10- to 40-bases primers for specific amplification of a gene that is defined by any one of the nucleotide sequences of SEQ ID NOS: 1 to 121 above; and/or at least one probe that is selected from 10- to 40-bases probes, which specifically hybridizes to a gene that is defined by any one of the nucleotide sequences of SEQ ID NOS: 1 to 121 above.

When the kit of the invention contains a primer, the kit may contain components of a reaction solution including a buffer, dNTP mixture, enzymes (e.g., reverse transcriptase and RNaseH), a standard sample for calibration, or the like. When the kit of the invention contains a probe, the kit may contain a hybridization buffer, a washing buffer, a microplate, a nylon membrane or the like. The kit may also contain primers for specific amplification of a housekeeping gene such as ubiquitin gene and/or a probe specifically hybridizing to a housekeeping gene.

EXAMPLE

Example 1

Wheat plants were grown outdoors until immediately before flowering and then grown within an artificial climate chamber at 15° C. On day 10 after flowering, some of the wheat plants were transferred to an environment at 20° C. or 10° C. and then grown under this environment until day 15 after flowering. On day 15 after flowering, some of immature seeds were harvested for use as samples for gene expression analysis. Some of the remaining plants were transferred to an environment at 15° C. The transferred seeds on day 50 after flowering were regarded as matured seeds and then subjected to component analysis.

Meanwhile, wheat plants were transferred into an artificial climate chamber during the flowering stage and then grown at 15° C. Some of the wheat plants were transferred to an environment at 20° C. or 10° C. on day 30 after flowering and then grown under this environment until day 35 after flowering. Some of immature seeds were harvested on day 35 after flowering for use as samples for gene expression analysis. Some of the remaining plants were transferred to an environment at 15° C. The transferred seeds on day 50 after flowering were regarded as matured seeds and then subjected to component analysis.

Expression analysis was carried out with a Hi-CEP (High Coverage Expression Profiling) method. The Hi-CEP method was developed by Abe et al., at the National Institute of Radiological Sciences (Fukumura R, Takahashi H, Saito T, Tsutsumi Y, Fujimori A, Sato S, Tatsumi K, Araki R, Abe M., Nucleic Acids Res. 2003, 15; 31(16): e94) and is composed of the following elements.

(1) mRNA Extraction

Total RNA was extracted from immature seeds of wheat that had been grown in a triple temperature zone with a SDS-phenol method. The seeds were milled, suspended in extraction buffer (100 mM Tris-HCl (pH 8.0), 10 mM EDTA (pH 8.0), 100 mM LiCl, and 1% SDS), and then subjected to phenol/chloroform treatment. After another phenol/chloroform treatment, LiCl precipitation was carried out. The precipitate was dissolved in 400 µl of DEPC-treated water, followed by phenol/chloroform treatment, chloroform treatment, and EtOH precipitation. After drying, the resultant was dissolved in 200 µl of 0.1 M sodium acetate (pH 6.0). 20 µl of EtOH was then added to precipitate and remove polysaccharides. The supernatant was precipitated with EtOH. After drying, the resultant was dissolved in DEPC-treated water. mRNA was purified from the solution using a Micro-Fast Track™ 2.0 mRNA Isolation Kit (produced by Invitrogen). The purification was carried out according to the manual included in the kit.

(2) Preparation of Templates for Selective PCR

Double-stranded cDNA was synthesized using oligo dT (5'-biotin-TTTTTTTTTTTTTTTTTTT-3') having biotin added to the 5' end as a primer and a Superscript™ Double-strand cDNA Synthesis Kit (produced by Invitrogen). The double-stranded cDNA was digested with a restriction enzyme MspI and then MspI adaptors (5'-AATGGCTACAC-GAACTCGGTTCATGACA-3' and 5'-CGTGTCATGAAC-CGAGTTCGTGTAGCCATT-3') were added. Fragments of the polyA side alone were collected using avidin magnetic particles (Dynabeads M-280 Streptavidin; produced by Dynal). Subsequently, digestion with a restriction enzyme MseI was carried out and then MseI adaptors (5'-AAG-TATCGTCACGAGGCGTCCTACTGCG-3' and 5'-TACG-CAGTAGGACGCCTCGTGACGATACTT-3') were added. Fragments of the polyA side were discarded using avidin magnetic particles. The remaining fragments were used as templates for the following selective PCR.

(3) Selective PCR Using 256 Types of Primer

Primers were designed to bind to the above adaptors and then PCR was carried out. At this time, an end of each primer was designed so that it protrudes from the cDNA fragment side by 2 nucleotides. PCR was carried out using a total of 16 patterns. Moreover, a primer of the MspI side was fluorescence-labeled with FAM. MspI-primer (5'-FAM-ACTCG-GTTCATGACACGGNN-3') and MseI-primer (5'-AG-GCGTCCTACTGCGTAANN-3') were used as fluorescent primers. PCR cycles carried out herein consisted of: 1 cycle of 95° C. for 1 minute; 28 cycles of 95° C. for 20 seconds, 71.5° C. for 30 seconds, and 72° C. for 1 minute; and 1 cycle of 60° C. for 30 minutes.

(4) Profile Comparison Among Samples and Selection of Fragments with Changed Expression Levels Each PCR product was diluted to an appropriate concentration. 10 μl of formamide and 0.3 μl of ROX marker (produced by Applied Biosystems) were added to 3 μl of the PCR product and then the PCR product was subjected to electrophoresis using ABI Prism 3100 (produced by Applied Biosystems). The results were analyzed using GeneScan 3.7 (produced by Applied Biosystems) so that fragments exhibiting changed expression levels could be selected.

(5) Determination of the Nucleotide Sequences of the Selected Fragments

Acrylamide gel was prepared on a 20×40 cm glass plate. PCR mixtures containing the fragments selected in (4) were subjected to electrophoresis, thereby excising target fragments. The excised fragments were suspended in 1×TE buffer. PCR was carried out using the suspensions as templates. It was confirmed whether the excised fragments were identical to the target fragments. Primers used herein were a MspI-universal T7 primer (5'-TAGGTAATACGACTCAC-TATAGGGCGAATTGGGTACTCGGTTCATGACAC GG-3') and a MseI-universal primer (5'-AGGCGTCCTACT-GCGTAA-3'). When a PCR product having the same molecular weight as that of a target fragment was obtained, the sequence was read by direct sequencing. At this time, a T7 primer (5'-TAATACGACTCACTATAGGG-3') was used.

Table 2 shows data obtained by the expression analysis. SEQ ID NOS: in Table 2 correspond to SEQ ID NOS: in the sequence listing. In columns for characteristics and ratio, behavior observed (increased or decreased expression level when the level is compared with the result of a control zone) and the ratio of change in the expression level when a subject is exposed to a temperature change during the ripening stage, as compared to the expression level of a control, are listed. Furthermore, as a result of homology search conducted at DDBJ (hosted by the National Institute of Genetics), genes having high homology, examples of ESTs and accession Nos. thereof are listed in Table 2.

TABLE 2

List of wheat genes exhibiting characteristic changes in expression as seslected by HiCEP method

| SEQ ID NO: | Examples of genes having high homology | Accession No. (Gene or EST) | Accession No. (Unigene) | Characteristics | Ratio |
|---|---|---|---|---|---|
| 1 | alpha-amylase gene | X05809 | | Expression was induced at low temperatures on Day 15 | 8.1 |
| 2 | germ agglutinin | J02961 | | Expression was induced at high temperatures on Day 15 | 13.1 |
| 3 | germ agglutinin isolectin D | M25537 | | Expression was induced at high temperatures on Day 15 | 22.2 |
| 4 | germ agglutinin isolectin A | M25536 | | Expression was induced at high temperatures on Day 15 | 22.1 |
| 5 | ADP-glucose pyrophosphorylase | X67151 | | Expression was suppressed at high temperatures on Day 35 | 0.08 |
| 6 | serpin WZS3 | Y11486 | | Expression was suppressed at low temperatures on Day 15 | 0.48 |
| 7 | protein disulfide isomerase | U11496 | | Expression was induced at low temperatures on Day 15 | 3.1 |
| 8 | catalase | X94352 | | Expression was suppressed at high temperatures on Day 15 | 0.15 |
| 9 | 60s ribosomal protein L21 | AF475114 | | Expression was suppressed at high temperatures on Day 15 | 0.13 |
| 10 | Em H2 | X73227 | | Expression was suppressed at high temperatures on Day 35 | 0.09 |
| 11 | root abundant protein | U91834 | | Expression was suppressed at high temperatures on Day 35 | 0.23 |

TABLE 2-continued

List of wheat genes exhibiting characteristic changes in expression as seslected by HiCEP method

| SEQ ID NO: | Examples of genes having high homology | Accession No. (Gene or EST) | Accession No. (Unigene) | Characteristics | Ratio |
|---|---|---|---|---|---|
| 12 | secretory protein | AF079526 | | Expression was suppressed at low temperatures on Day 15 | 0.37 |
| 13 | glucose and ribitol dehydrogenase homolog | S72926 | | Expression was induced at high temperatures on Day 15 | 4.0 |
| 14 | alpha-amylase tetrameric inhibitor CM3 | X61032 | | Expression was induced at high temperatures on Day 15 | 2.9 |
| 15 | PST19, LRR19, TAK19-1, and LRK19 genes | AF325196 | | Expression was suppressed at high temperatures on Day 35 | 0.08 |
| 16 | Acc1 | AF029897 | | Expression was induced at high temperatures on Day 35 | 30.1 |
| 17 | PDI3 AF262981 | U11496 | | Expression was induced at low temperatures on Day 15 | 3.1 |
| 18 | Histon H3 gene | X00937 | | Expression was induced at low temperatures on Day 15 | 3.1 |
| 19 | EC protein | X68288 | | Expression was induced at high temperatures on Day 15 | 5.3 |
| 20 | γ-gliadin gene | M16064 | | Expression was induced at high temperatures on Day 15 | 3.0 |
| 21 | WPR4a 4b | AJ006099 | | Expression was induced at high temperatures on Day 15 | 5.0 |
| 22 | nodulin-like protein | CN012339 | Ta.28330 | Expression was suppressed at low temperatures on Day 15 | 0.17 |
| 23 | ADP-glucose pyrophosophorylase | CD909202 | Ta.2797 | Expression was suppressed at high temperatures on Day 15 | 0.08 |
| 24 | Gamma-thionin homolog | CA701480 | Ta.27389 | Expression was suppressed at high temperatures on Day 35 | 0.05 |
| 25 | hydroxymethylglutaryl-CoA lyase | CD453645 | Ta.8391 | Expression was suppressed at low temperatures on Day 15 | 0.56 |
| 26 | nodulin-like protein | BG313072 | Ta.21043 | Expression was suppressed at low temperatures on Day 15 | 0.26 |
| 27 | nodulin-like protein | BQ579734 | Ta.9559 | Expression was suppressed at low temperatures on Day 15 | 0.35 |
| 28 | O-methyltransferase-like protein | CD896263 | Ta.11022 | Expression was suppressed at low temperatures on Day 15 | 0.28 |
| 29 | putative carboxyl-terminal peptidase | BE422634 | Ta.1234 | Expression was suppressed at high temperatures on Day 15 | 0.15 |
| 30 | plasma membrane intrinsic protein 1 | CN011928 | Ta.1013 | Expression was induced at high temperatures on Day 15 | 4.7 |
| 31 | putative phosphoprotein phosphatase | BE419998 | Ta.29303 | Expression was induced at high temperatures on Day 15 | 4.8 |
| 32 | cytochrome P450, putative | BJ297614 | Ta.5864 | Expression was induced at high temperatures on Day 15 | 4.6 |
| 33 | 3(2),5-bisphosphate nucleotidase | BG909591 | Ta.3052 | Expression was suppressed at high temperatures on Day 35 | 0.10 |
| 34 | alpha/beta-gliadin | BJ293268 | Ta.24528 | Expression was suppressed at low temperatures on Day 15 | 0.34 |
| 35 | latex allergen from *Hevea brasiliensis* | CD453773 | Ta.28866 | Expression was suppressed at high temperatures on Day 15 | 0.30 |

TABLE 2-continued

List of wheat genes exhibiting characteristic changes in expression as seslected by HiCEP method

| SEQ ID NO: | Examples of genes having high homology | Accession No. (Gene or EST) | Accession No. (Uni-gene) | Characteristics | Ratio |
|---|---|---|---|---|---|
| 36 | photosystem II type I chlorophyll a b binding protein | BQ619858 | Ta.22984 | Expression was suppressed at high temperatures on Day 15 | 0.27 |
| 37 | glucose-6-phosphate dehydrogenase | AL813188 | Os.16992 | Expression was suppressed at low temperatures on Day 15 | 0.34 |
| 38 | heat shock protein | BJ296904 | Ta.1471 | Expression was suppressed at low temperatures on Day 35 | 0.45 |
| 39 | calnexin-like protein | CK210625 | Ta.2538 | Expression was suppressed at low temperatures on Day 35 | 0.4 |
| 40 | phosphatase 2C-like protein | CD920796 | Ta.5734 | Expression was suppressed at high temperatures on Day 35 | 0.13 |
| 41 | glutathione S-transferase | CD934218 | Ta.240 | Expression was suppressed at high temperatures on Day 35 | 0.25 |
| 42 | filamentous flower protein | BE402267 | Ta.14101 | Expression was suppressed at high temperatures on Day 35 | 0.25 |
| 43 | dynein light subunit 1c6, flagellar outer arm | CA639052 | Ta.18579 | Expression was suppressed at high temperatures on Day 35 | 0.19 |
| 44 | ribosomal protein S15-like protein | BJ222598 | Ta.20582 | Expression was induced at high temperatures on Day 35 | 2.5 |
| 45 | gamma-gliadin | BE423434 | | Expression was suppressed at low temperatures on Day 15 | 0.36 |
| 46 | berberine bridge enzyme-like protein | BQ166952 | Ta.10981 | Expression was induced at low temperatures on Day 15 | 2.2 |
| 47 | Chalcone synthase | CA704178 | Ta.10418 | Expression was induced at low temperatures on Day 15 | 2.1 |
| 48 | 70 kDa heat shock protein | CD912041 | AF005993 | Expression was suppressed at low temperatures on Day 15 | 0.25 |
| 49 | subtilisin-like proteinase | CD373689 | Ta.24597 | Expression was suppressed at high temperatures on Day 15 | 0.34 |
| 50 | photosystem-I PSI-F subunit precursor | BE426533 | U08135 | Expression was suppressed at high temperatures on Day 15 | 0.56 |
| 51 | putative ribosomal protein S14 | CN011733 | Ta.3522 | Expression was suppressed at high temperatures on Day 15 | 0.25 |
| 52 | 70 kDa heat shock protein | CD912041 | AF005993 | Expression was induced at high temperatures on Day 15 | 2.7 |
| 53 | O-methyltransferase-like protein | CD919815 | Ta.5951 | Expression was suppressed at low temperatures on Day 35 | 0.05 |
| 54 | nodulin-like protein | CD896425 | Ta.5650 | Expression was induced at low temperatures on Day 35 | 5.3 |
| 55 | ABC transporter-like protein | CD881710 | Os.6118 | Expression was induced at high temperatures on Day 35 | 4.2 |
| 56 | expressed protein | AJ615971 | Os.11603 | Expression was induced at high temperatures on Day 15 | 9.4 |
| 57 | expressed protein | BE499562 | Ta.9230 | Expression was suppressed at high temperatures on Day 35 | 0.24 |
| 58 | expressed protein | CD899928 | Ta.18615 | Expression was suppressed at low temperatures on Day 35 | 0.36 |
| 59 | expressed protein | BJ261310 | Ta.1519 | Expression was suppressed at high temperatures on Day 35 | 0.15 |

TABLE 2-continued

List of wheat genes exhibiting characteristic changes in expression as seslected by HiCEP method

| SEQ ID NO: | Examples of genes having high homology | Accession No. (Gene or EST) | Accession No. (Unigene) | Characteristics | Ratio |
|---|---|---|---|---|---|
| 60 | expressed protein | CA595676 | Os.18152 | Expression was suppressed at high temperatures on Day 35 | 0.09 |
| 61 | expressed protein | BE515838 | Os.18152 | Expression was suppressed at high temperatures on Day 35 | 0.18 |
| 62 | expressed protein | CD902303 | Ta.28185 | Expression was induced at high temperatures on Day 15 | 3.0 |
| 63 | expressed protein | BE446498 | Ta.14087 | Expression was induced at low temperatures on Day 35 | 5.8 |
| 64 | expressed protein | AL815606 | Ta.10329 | Expression was induced at low temperatures on Day 35 | 12 |
| 65 | unknown protein | CD885342 | Os.18095 | Expression was induced at low temperatures on Day 35 | 5.1 |
| 66 | unknown protein | CD917189 | Ta.9344 | Expression was induced at low temperatures on Day 35 | 2.7 |
| 67 | unknown protein | BJ267693 | | Expression was induced at low temperatures on Day 15 | 2.8 |
| 68 | hypothetical protein | CD920596 | Ta.14510 | Expression was suppressed at low temperatures on Day 15 | 0.24 |
| 69 | hypothetical protein | CD925669 | Ta.13739 | Expression was induced at high temperatures on Day 15 | 10.6 |
| 70 | hypothetical protein | BQ483298 | Ta.7782 | Expression was suppressed at high temperatures on Day 35 | 0.02 |
| 71 | hypothetical protein | CA720103 | Os.18496 | Expression was suppressed at high temperatures on Day 35 | 0.30 |
| 72 | hypothetical protein | CD912035 | Ta.14111 | Expression was suppressed at low temperatures on Day 15 | 0.42 |
| 73 | hypothetical protein | CA640372 | Os.28192 | Expression was suppressed at low temperatures on Day 15 | 0.40 |
| 74 | hypothetical protein | CD912035 | Ta.14111 | Expression was suppressed at low temperatures on Day 15 | 0.63 |
| 75 | hypothetical protein | CD893664 | Ta.837 | Expression was suppressed at high temperatures on Day 15 | 0.16 |
| 76 | putative protein | CD917477 | Ta.13237 | Expression was induced at low temperatures on Day 35 | 10.5 |
| 77 | putative protein | CD920503 | Os.4124 | Expression was suppressed at low temperatures on Day 35 | 0.4 |
| 78 | putative protein | BJ272522 | Ta.13392 | Expression was suppressed at high temperatures on Day 35 | 0.31 |
| 79 | putative protein | CD887715 | Ta.7485 | Expression was induced at high temperatures on Day 35 | 2.6 |
| 80 | putative protein | AL820153 | Os.13027 | Expression was induced at high temperatures on Day 35 | 2.3 |
| 81 | putative protein | CD917477 | Ta.13237 | Expression was induced at low temperatures on Day 35 | 11.6 |
| 82 | unknown | BQ246884 | | Expression was induced at low temperatures on Day 15 | 7.5 |
| 83 | unknown | CK218032 | Ta.26929 | Expression was suppressed at low temperatures on Day 35 | 0.15 |

TABLE 2-continued

List of wheat genes exhibiting characteristic changes in expression as seslected by HiCEP method

| SEQ ID NO: | Examples of genes having high homology | Accession No. (Gene or EST) | Accession No. (Unigene) | Characteristics | Ratio |
|---|---|---|---|---|---|
| 84 | unknown | CD899270 | | Expression was induced at low temperatures on Day 15 | 5.4 |
| 85 | unknown | BQ657889 | | Expression was induced at low temperatures on Day 15 | 7.8 |
| 86 | unknown | CD886964 | Hv. 6473 | Expression was suppressed at high temperatures on Day 15 | 0.13 |
| 87 | unknown | BE606284 | | Expression was suppressed at low temperatures on Day 35 | 0.37 |
| 88 | unknown | BJ304521 | Ta.6418 | Expression was suppressed at low temperatures on Day 35 | 0.23 |
| 89 | unknown | CD924903 | | Expression was suppressed at low temperatures on Day 35 | 0.27 |
| 90 | unknown | CD924903 | | Expression was suppressed at low temperatures on Day 35 | 0.3 |
| 91 | unknown | BJ289636 | Ta.5785 | Expression was suppressed at low temperatures on Day 35 | 0.22 |
| 92 | unknown | BJ296338 | Ta.6135 | Expression was suppressed at low temperatures on Day 35 | 0.4 |
| 93 | unknown | BJ304247 | Ta.9474 | Expression was suppressed at high temperatures on Day 35 | 0.12 |
| 94 | unknown | CA635718 | Ta.7698 | Expression was suppressed at low temperatures on Day 15 | 0.43 |
| 95 | unknown | CD933817 | Ta.9952 | Expression was induced at low temperatures on Day 15 | 2.8 |
| 96 | unknown | BQ167139 | Ta.9952 | Expression was induced at low temperatures on Day 15 | 2.3 |
| 97 | unknown | BE517536 | Ta.3563 | Expression was induced at high temperatures on Day 15 | 2.0 |
| 98 | unknown | CA734406 | | Expression was suppressed at high temperatures on Day 15 | 0.37 |
| 99 | unknown | CD902294 | | Expression was suppressed at low temperatures on Day 35 | 0.33 |
| 100 | unknown | CA674723 | Ta.23005 | Expression was induced at low temperatures on Day 35 | 3.2 |
| 101 | unknown | CA706528 | | Expression was induced at low temperatures on Day 35 | 4.2 |
| 102 | unknown | CD921040 | | Expression was suppressed at high temperatures on Day 35 | 0.33 |
| 103 | unknown | CD924903 | | Expression was suppressed at high temperatures on Day 35 | 0.24 |
| 104 | unknown | CD924903 | | Expression was suppressed at high temperatures on Day 35 | 0.20 |
| 105 | unknown | BE424430 | Ta.27947 | Expression was suppressed at high temperatures on Day 35 | 0.37 |

TABLE 2-continued

List of wheat genes exhibiting characteristic changes in expression as seslected by HiCEP method

| SEQ ID NO: | Examples of genes having high homology | Accession No. (Gene or EST) | Accession No. (Unigene) | Characteristics | Ratio |
|---|---|---|---|---|---|
| 106 | unknown | CA741187 | Ta.22349 | Expression was suppressed at high temperatures on Day 35 | 0.29 |
| 107 | unknown | CK161796 | | Expression was induced at high temperatures on Day 35 | 3.60 |
| 108 | unknown | CD887242 | | Expression was induced at high temperatures on Day 35 | 3.3 |
| 109 | unknown | BF483601 | Ta.1834 | Expression was suppressed at high temperatures on Day 35 | 0.27 |
| 110 | unknown | BQ237369 | | Expression was induced at low temperatures on Day 15 | 9.0 |
| 111 | unknown | CD886964 | | Expression was induced at low temperatures on Day 15 | 2.1 |
| 112 | unknown | CD922259 | | Expression was suppressed at low temperatures on Day 15 | 0.31 |
| 113 | unknown | BE431054 | Ta.25056 | Expression was suppressed at high temperatures on Day 15 | 0.38 |
| 114 | unknown | CA741187 | Ta.22349 | Expression was suppressed at high temperatures on Day 15 | 0.29 |
| 115 | unknown | CD894232 | | Expression was suppressed at high temperatures on Day 15 | 0.21 |
| 116 | unknown | BQ170549 | | Expression was suppressed at high temperatures on Day 15 | 0.32 |
| 117 | unknown | BE517536 | Ta.3563 | Expression was induced at high temperatures on Day 15 | 2.4 |
| 118 | unknown | CD908140 | | Expression was induced at high temperatures on Day 35 | 2.0 |
| 119 | unknown | AL810525 | | Expression was induced at high temperatures on Day 35 | 3.5 |
| 120 | unknown | BQ904799 | | Expression was induced at high temperatures on Day 35 | 1.8 |
| 121 | unknown | CD904365 | Ta.10020 | Expression was induced at low temperatures on Day 35 | 3.7 |

Example 2

From the genes having high homology with known genes as confirmed by homology search included the genes listed in Table 2, 5 genes were selected. These genes were the gene (SEQ ID NO: 1) encoding α-amylase, the gene (SEQ ID NO: 8) encoding catalase, the gene (SEQ ID NO: 34) encoding α-, β-gliadin, the gene (SEQ ID NO: 48) encoding a heat shock protein (70 kDa), and the gene (SEQ ID NO: 45) encoding γ-gliadin. The expression levels of these target genes in wheat (T. aestivum L.) seeds on day 15 after flowering were quantified. Primers and a probe for quantitative real-time PCR were designed within each target gene using genetic analysis software Primer Express Ver. 2. The sequences are listed in Table 3.

TABLE 3

Combinations of primers and probes used for reverse transcription quantitative PCR

| SEQ ID NO: | Primer 1 | Primer 2 | Fluorescence-labeled probe |
|---|---|---|---|
| 1 | GGCCGAGGGCGATCTC | GGCCACTCTTCTCCCAGAC | FAM-ATCCCCTCGGGTTTCA |
| 8 | GCTCAAGATGAAGCCGAACATG | TTCATGCTGCACCCTCCTT | FAM-TCGACCGACGCCAACC |

TABLE 3-continued

Combinations of primers and probes used for
reverse transcription quantitative PCR

| SEQ ID NO: | Primer 1 | Primer 2 | Fluorescence-labeled probe |
|---|---|---|---|
| 34 | GCCGTAGCTTACCAGTAACCA | GATTTGTACACCAACACCCAGAAG | FAM-CCGCATGACAAATAA |
| 48 | GGTCCCTGGCAGTGGTACT | CTAGGTGTACATCATTCCCTCGAAA | FAM-CATCCTGCGTTATTCG |
| 45 | GATGGCTCCGATCCCTATGTAG | CCGAATGGAAACACGCGGATA | FAM-ACGCTATATGCAGAAAAT |

Wheat plants were grown outdoors until immediately before flowering and then transferred into an artificial climate chamber. The environmental temperature within the chamber was maintained at 15° C. On day 10 after flowering, some of the wheat plants were transferred into a room with a room temperature of 10° C. or 20° C. On day 15 after flowering, some of the immature seeds were harvested. The remaining pots were transferred into an environment at 15° C. and then the seeds of transferred wheat plants were harvested on day 40 after flowering. Total RNA was extracted from the immature seeds. The extraction was carried out according to the following procedures.

Approximately 500 mg of wheat seeds was finely milled. The milled flour was mixed with 12 ml of extraction buffer (100 mM Tris-HCl (pH 8.0), 10 mM EDTA (pH 8.0), 100 mM LiCl, and 1% SDS) and 8 ml of TE (pH 8.0) saturated phenol/chloroform. Centrifugation (8,000×g for 30 minutes) was then carried out. An equivalent volume of TE (pH 8.0) saturated phenol/chloroform/isoamyl alcohol (25:24:1) was added to the upper layer, followed by centrifugation (8,000×g for 30 minutes). 10 M LiCl was added in a ⅓ volume to the upper layer, followed by centrifugation (8,000×g for 30 minutes). The resultant was allowed to stand at −20° C. for 1 hour, centrifugation (8,000×g for 30 minutes) was carried out, and then the precipitate was suspended in 5 ml of 2 M LiCl. The centrifugation (8,000×g for 15 minutes) was carried out and then the precipitate was suspended in 400 µl of DEPC-treated water. An equivalent volume of TE (pH 8.0) saturated phenol/chloroform/isoamyl alcohol (25:24:1) was added, followed by centrifugation (8,000×g for 10 minutes). An equivalent volume of TE (pH 8.0) saturated chloroform/isoamyl alcohol (24:1) was added to the upper layer, followed by centrifugation (8,000×g for 10 minutes). 3 M NaOAc (pH 5.2) and EtOH were added in a ⅒ volume and a 2.5-fold volume, respectively, to the upper layer, followed by centrifugation (8,000×g for 10 minutes). The precipitate was dissolved in 200 µl of 0.1 M sodium acetate (pH 6.0). 20 µl of EtOH was slowly added dropwise, followed by centrifugation (8,000×g for 10 minutes). EtOH was added in a 2.5-fold volume to the supernatant, followed by centrifugation (8,000×g for 10 minutes). The precipitate was washed with 1 ml of 70% EtOH (30% DEPC-treated water), followed by centrifugation (8,000×g for 10 minutes).

The precipitate was dried in a desiccator and then dissolved in 100 µl of DEPC-treated water. The extracted RNA was subjected to electrophoresis using modified gel and soundness was evaluated based on the presence of ribosome RNA. Concentrations were measured using a spectrophotometer in preparation for reverse transcription real-time PCR.

cDNAs were synthesized using total RNAs as templates using a Superscript™ Double-strand cDNA Synthesis Kit (produced by Invitrogen). Synthesis was carried out according to the manual included in the kit. Oligo-dT primers were used as primers.

Ubiquitin gene was used as an internal standard whose expression level does not change depending on tissues or growth stages. The quantitative PCR for the internal standard was carried out using several concentrations of cDNA solution, so that a calibration curve was obtained and an appropriate concentration width was determined. A solution with the most appropriate concentration was used as a template for the quantitative PCR for each target. The quantitative PCR was carried out using a 96-well plate. 4 wells were used for each sample. The reaction solution composition in each well is shown in Table 4.

TABLE 4

Composition of reverse transcription quantitative PCR reaction solution

| Reagent | For ubiquitin (standard gene) | For target gene |
|---|---|---|
| Template (cDNA) | 1 µl | 1 µl |
| 2X TaqMan Universal Master Mix | 10 µl | 10 µl |
| 20X TaqMan Primer & probe Mix |  | 1 µl |
| Ubiquitin F Primer (18 µM) | 1 µl |  |
| Ubiquitin R Primer (18 µM) | 1 µl |  |
| Ubiquitin probe (5 µM) | 1 µl |  |
| dDW | 6 µl | 8 µl |
| Total | 20 µl | 20 µl |

The quantitative PCR was carried out using an ABI PRISM 7700 Sequence detector. PCR cycles carried out herein consisted of: 50° C. for 2 minutes, 95° C. for 10 minutes, and 40 cycles of 95° C. for 15 seconds and 60° C. for 1 minute. The results were standardized using 18s ribosomal RNA.

Finally, the characteristics of starch and protein in the harvested matured wheat seeds were analyzed. Items analyzed were amylose content, amylopectin side-chain length, protein content, and ratio of glutenin level to gliadin level. Measurement methods employed for these items are each described below.

Amylose Content

Dough was made by adding a small amount of water to milled matured wheat seeds and then kneading the resultant in water, thereby obtaining gluten alone. The remaining starch suspension was centrifuged. The precipitate was dried and then used for each starch sample. Amylose contents were measured according to the method of Williams et al. (Williams, P. C., Kuzina, F. D., and Hlynak, I. (1970) Cereal Chem. 47: 411-420)). The water content of the sample was measured, and then approximately 100 mg of the sample was precisely weighed. 1 ml of 95% EtOH and 9 ml of 1 N NaOH were added to the sample, and then the sample was heated in hot water for 10 minutes. The sample was then cooled to room temperature and then a starch solution was collected in another container while washing it with water. The container was filled up to contain 100 ml of the solution and then 1 ml of 1 M AcOH and 2 ml of an iodine solution were added thereto. After the solution was mixed well, it was allowed to stand for 20 minutes and then absorbance was measured at 620 nm using a spectrophotometer. A calibration curve was obtained using potato amylose and amylopectin, and then the amylose content of each sample was determined.

Analysis of Amylopectin Side-chain Length Distribution

According to the method of Koizumi et al. (Koizumi, K., Fukuda, M., and Hizukuri, S. (1991) J. Chromatogr. 585:233-238), the distribution of amylopectin side-chain lengths was analyzed. Each starch sample was treated with hot methanol, so as to deactivate amylase. The sample was then suspended in water and treated at 100° C. for 1 hour to gelatinize the sample. The sample was subjected to isoamylase treatment in acetate buffer (pH 4.5) (40° C. for 8 hours). After addition of the enzyme, the sample was also treated for another 16 hours. After deactivation in boiling water, the distribution of the side chains was determined by HPAEC. Each starch sample subjected to isoamylase treatment was dissolved in 0.4 M NaOH, filtrated to remove contaminants using filters, and then subjected to anion exchange chromatography (HPAE-PAD: High Performance Anion Exchange Chromatography with Pulsed Amperometric Detection) in a system provided with a titrator for pulsed current. Glucose, maltose, maltotriose, maltotetraose, and the like were similarly subjected to HPAE-PAD as controls. Amylopectin chain lengths of the samples were compared.

Measurement of Starch Gelatinization Temperature

Measurement was carried out according to the techniques of Hayakawa et al. (Hayakawa, K., Tanaka, K., Nakamura, T., Endo, S., and Hoshino, T. (1997) Cereal Chem. 74 (5): 576-580). Starch gelatinization peak temperatures were measured using a DSC (differential scanning calorimeter). 10 mg of starch was placed on a silver pan exclusively used for DSC, 40 μl of distilled water was added thereto, and then the cover was sealed. The temperature was raised from 25° C. to 150° C. at a constant rate (5° C. per minute). Endothermic changes that had taken place with starch gelatinization were measured. Gelatinization peak temperatures (Tp) were measured as gelatinization temperatures.

Crude Protein Content

Crude protein content was measured by a generally well-known Kjeldahl decomposition method. After hydrolysis of milled matured wheat seeds, free nitrogen was determined. The result was multiplied by a protein conversion factor of 5.7 to obtain crude protein content.

Measurement of the Ratio of Glutenin to Gliadin

The measurement was carried out according to the method of Blumenthal et al. (Blumenthal, C., Bekes, F., Gras, P. W., Barlow, W. R., and Wrigley, C. W. (1995) Cereal Chem. 72(6): 539-544). Specifically, proteins were extracted from milled matured wheat seeds without using any reducing agent. The extracted proteins were suspended in phosphate buffer containing SDS (sodium dodecyl sulfate) and then sufficiently dissolved by ultrasonication. After filtration using filters, the resultants were subjected to size-exclusion HPLC. The first peak was defined as indicating aggregated glutenin and the second peak was defined as indicating non-aggregated gliadin. An area ratio was calculated as the ratio of glutenin to gliadin.

The results of the experiments are listed in Tables 5 and 6.

TABLE 5

Changes in gene expression levels in immature seeds when environmental temperatures were varied during the ripening stage

| Reverse transcription quantitative PCR | | Low temperature treatment | High temperature treatment |
|---|---|---|---|
| SEQ ID NO: | Gene having high homology | Expression level relative to the expression level of ubiquitin gene | |
| 1 | α-amylase | 1.7 times | 0.084 times |
| 8 | Catalase | 3.2 times | 1.4 times |

TABLE 5-continued

Changes in gene expression levels in immature seeds when environmental temperatures were varied during the ripening stage

| Reverse transcription quantitative PCR | | Low temperature treatment | High temperature treatment |
|---|---|---|---|
| SEQ ID NO: | Gene having high homology | Expression level relative to the expression level of ubiquitin gene | |
| 34 | α-, β-gliadin | 0.45 times | 1.4 times |
| 48 | Heat shock protein 70 kDa | 0.036 times | 0.32 times |
| 45 | γ-gliadin | 0.0015 times | 0.0033 times |

TABLE 6

Analytical results of the end use qualities of matured seeds when environmental temperatures were varied during the ripening stage

| Item measured | Low temperature treatment | High temperature treatment | Control |
|---|---|---|---|
| Amylose content (%) | 22.5 | 24.5 | 23.0 |
| Amylopectin side-chain DP6-12 percentage (%) | 32.6 | 27.5 | 31.7 |
| Gelatinization temperature (° C.) | 61.4 | 63.3 | 62.5 |
| Crude protein content (%) | 9.7 | 11.0 | 10.0 |
| Ratio of glutenin to gliadin | 0.70 | 0.64 | 0.68 |

Example 3

Some immature seeds of domestically grown wheat for noodles were harvested on days 15 to 20 after flowering. Meanwhile, matured seeds were harvested. Total RNAs were extracted from the immature seeds according to the procedures in Example 2. After concentrations were measured using a spectrophotometer, cDNAs were synthesized by a similar method and then subjected to quantitative real-time PCR.

Quantitative real-time PCR was carried out. The expression levels of 5 genes relative to the expression level of ubiquitin gene were determined. The results are shown in Table 7.

TABLE 7

Relative gene expression levels in immature seeds

| SEQ ID NO: | Gene having high homology | Expression level relative to the expression level of ubiquitin gene |
|---|---|---|
| 1 | α-amylase | 1.4 times |
| 8 | Catalase | 4.8 times |
| 34 | α-, β-gliadin | 0.3 times |
| 48 | Heat shock protein 70 kDa | 0.012 times |
| 45 | γ-gliadin | 0.00012 times |

The gene expression pattern shown in Table 7 was analogous to that in the case of wheat exposed to low temperatures during the ripening stage. Therefore, it was predicted that mature seeds to be obtained from the wheat would possess the characteristics listed in Table 1; that is, short amylopectin side-chain length, low starch gelatinization temperature, and lower-molecular-weight amylose and amylopectin.

According to the method in Example 2, component analysis was conducted for seeds harvested after full maturation. The result demonstrated that harvested matured seeds possessed characteristics as predicted (Table 8). Therefore, it was revealed that the end use qualities of wheat flour obtained from matured seeds that will be harvested in the future can be estimated by evaluating the expression levels of the above 5 genes in the seeds during their ripening stage.

TABLE 8

Analytical results of the qualities of matured seeds

| Item measured | Analytical value | Seeds grown at 15° C. |
|---|---|---|
| Amylose content (%) | 22.1 | 23.0 |
| Mean amylopectin side-chain length (DP) | 32.9 | 31.7 |
| Gelatinization temperature (° C.) | 61.1 | 62.5 |
| Crude protein content (%) | 9.5 | 10.0 |
| Ratio of glutenin to gliadin | 0.71 | 0.68 |

Example 4

Some immature seeds of home-grown wheat were harvested on roughly days 20 to 30 after flowering. Matured seeds after harvest were also sampled. Total RNAs were extracted from the immature seeds according to the procedures described in control experiments. After concentrations were measured using a spectrophotometer, cDNAs were synthesized by a similar method and then subjected to quantitative real-time PCR. As a result of quantitative real-time PCR, the expression levels relative to the expression level of ubiquitin gene were as shown in Table 9.

TABLE 9

Relative gene expression levels in immature seeds

| SEQ ID NO: | Gene having high homology | Expression level relative to the expression level of ubiquitin gene |
|---|---|---|
| 1 | α-amylase | 0.096 times |
| 8 | Catalase | 1.9 times |
| 34 | α-, β-gliadin | 1.6 times |
| 48 | Heat shock protein 70 kDa | 0.5 times |
| 45 | γ-gliadin | 0.0042 times |

The gene expression pattern shown in Table 9 was analogous to that in the case of wheat exposed to high temperatures during the ripening stage. Therefore, it was predicted that mature seeds obtained from the wheat would possess the characteristics listed in Table 1; that is, high amylose content, long amylopectin side-chain length, high starch gelatinization temperature, high protein content, low ratio of glutenin to gliadin, and low levels of a large glutenin polymer.

According to the method in Example 2, component analysis was conducted for seeds harvested after full maturation. As a result, it was demonstrated that harvested matured seeds possessed the characteristics as predicted (Table 10). Therefore, it was revealed that the end use qualities of wheat flour obtained from matured seeds that will be harvested in the future can be estimated by evaluating the expression levels of the above 5 genes in the seeds during their ripening stage.

TABLE 10

Analytical results of the qualities of matured seeds

| Item measured | Analytical value | Seeds grown at 15° C. |
|---|---|---|
| Amylose content (%) | 24.8 | 23.0 |
| Mean amylopectin side-chain length (DP) | 27.9 | 31.7 |
| Gelatinization temperature (° C.) | 63.5 | 62.5 |
| Crude protein content (%) | 10.9 | 10.0 |
| Ratio of glutenin to gliadin | 0.64 | 0.68 |

INDUSTRIAL APPLICABILITY

The invention makes it possible to estimate the end use qualities of matured wheat seeds that will be obtained in the future at an early stage before maturation of the wheat seeds. Therefore, the risk of purchasing low-quality wheat can be reduced.

All publications, patents, and patent applications cited herein are incorporated herein by reference in their entirety.

The invention claimed is:

1. A method for estimating the end use qualities of a mature wheat seed, the method comprising:

a) harvesting immature wheat seeds on the $5^{th}$ to 35th day after flowering;

b) extracting RNA from the seeds;

c) measuring expression levels of at least five genes expressed in the seeds, the five genes with sequences comprising SEQ ID NO: 1, 8, 34, 48 and 45;

d) estimating the values of the following parameters in the mature wheat seeds based on the detected expression levels of said five genes: amylose content (%), mean amylopectin side-chain length (DP), gelatinization temperature, crude protein content (%) and ratio of glutenin to gliadin.

2. The method according to claim 1, wherein the expression level of a gene is measured by a reverse transcription quantitative PCR.

* * * * *